(12) United States Patent
Tamir

(10) Patent No.: US 10,279,510 B2
(45) Date of Patent: May 7, 2019

(54) METHOD OF SEPARATING WASTE MATERIAL

(71) Applicant: Infimer Technologies Ltd., Moshav Avihayil (IL)

(72) Inventor: Yuval Tamir, Moshav Avihayil (IL)

(73) Assignee: Infimer Technologies Ltd., Moshav Avihayil (IL)

( * ) Notice: Subject to any disclaimer, the term of this patent is extended or adjusted under 35 U.S.C. 154(b) by 102 days.

(21) Appl. No.: 15/309,805

(22) PCT Filed: May 11, 2015

(86) PCT No.: PCT/IL2015/050493
§ 371 (c)(1),
(2) Date: Nov. 9, 2016

(87) PCT Pub. No.: WO2015/173807
PCT Pub. Date: Nov. 19, 2015

(65) Prior Publication Data
US 2017/0182500 A1    Jun. 29, 2017

Related U.S. Application Data

(60) Provisional application No. 61/991,586, filed on May 11, 2014.

(51) Int. Cl.
*B29B 17/02* (2006.01)
*B03B 5/28* (2006.01)
(Continued)

(52) U.S. Cl.
CPC .............. *B29B 17/02* (2013.01); *B02C 23/18* (2013.01); *B03B 5/28* (2013.01); *B03B 9/06* (2013.01);
(Continued)

(58) Field of Classification Search
CPC .. B02C 23/18; B03B 5/28; B03B 9/06; B29B 17/02; B29B 17/042; B29B 2017/0244;
(Continued)

(56) References Cited

U.S. PATENT DOCUMENTS 3,850,771 A    11/1974  Penque
4,013,616 A     3/1977  Wallace
(Continued)

FOREIGN PATENT DOCUMENTS

AU         524220      9/1982
AU        9348165      4/1994
(Continued)

OTHER PUBLICATIONS

Written Opinion dated Jul. 26, 2018 From the Intellectual Property Office of Singapore, IPOS Re. Application No. 11201609466U. (11 Pages).
(Continued)

*Primary Examiner* — Frances Tischler

(57) ABSTRACT

A method of separating waste material to a plurality of separated materials is disclosed herein. The method is effected by subjecting the waste material to a separation according to specific gravity, to thereby obtain two or more fractions, and optionally subjecting one or more of said fractions to additional separation procedures, to thereby obtain two or more of a low-density polymeric material, a high-density polymeric material, a metal, a glass, an oil, and lignocelluloses. The disclosed method can further be effected by processing one or more of the separated materials to thereby obtain one or more processed materials of a beneficial use. Further disclose herein are separated and/or processed materials obtainable by the method, articles-of-manufacturing comprising same, and systems for separating and/or processing the waste material.

33 Claims, 5 Drawing Sheets

(51) Int. Cl.
*B03B 9/06* (2006.01)
*B02C 23/18* (2006.01)
*C12M 1/107* (2006.01)
*C12M 1/00* (2006.01)
*C12M 1/26* (2006.01)
*C12M 1/34* (2006.01)
*C12P 7/10* (2006.01)
*C12P 7/64* (2006.01)
*B29B 17/04* (2006.01)

(52) U.S. Cl.
CPC ......... *B29B 17/0412* (2013.01); *C12M 21/04* (2013.01); *C12M 21/12* (2013.01); *C12M 33/22* (2013.01); *C12M 41/12* (2013.01); *C12M 47/10* (2013.01); *C12P 7/10* (2013.01); *C12P 7/649* (2013.01); *B29B 2017/0244* (2013.01); *Y02E 50/16* (2013.01); *Y02E 50/343* (2013.01); *Y02W 30/47* (2015.05); *Y02W 30/524* (2015.05); *Y02W 30/622* (2015.05)

(58) Field of Classification Search
CPC ...... C12M 21/04; C12M 21/12; C12M 33/22; C12M 41/12; C12M 47/10; C12P 7/10; C12P 7/649; Y02E 50/343; Y02W 30/47; Y02W 30/524; Y02W 30/622
See application file for complete search history.

(56) References Cited

U.S. PATENT DOCUMENTS

| | | | |
|---|---|---|---|
| 4,772,430 A | 9/1988 | Sauda et al. | |
| 4,849,116 A | 7/1989 | Weinmann et al. | |
| 4,968,463 A | 11/1990 | Levasseur | |
| 4,992,605 A | 2/1991 | Craig et al. | |
| 5,033,860 A | 7/1991 | Nakamura | |
| 5,104,047 A | 4/1992 | Simmons | |
| 5,217,655 A | 6/1993 | Schmidt | |
| 5,269,947 A | 12/1993 | Baskis | |
| 5,705,722 A | 1/1998 | Monnier et al. | |
| 6,017,475 A | 1/2000 | Cantrell | |
| 6,024,226 A * | 2/2000 | Olivier | B03B 5/30 209/172.5 |
| 6,253,527 B1 | 7/2001 | De Zen | |
| 6,335,376 B1 | 1/2002 | Allen, III et al. | |
| 6,368,500 B1 | 4/2002 | Asa et al. | |
| 6,423,254 B1 | 7/2002 | Bertoglio | |
| 7,497,335 B2 | 3/2009 | Bork et al. | |
| 8,142,527 B2 | 3/2012 | Herskowitz et al. | |
| 8,859,832 B2 | 10/2014 | Myllyoja et al. | |
| 2003/0030176 A1 | 2/2003 | Monovoukas et al. | |
| 2004/0080072 A1 | 4/2004 | Bouldin et al. | |
| 2004/0192980 A1 | 9/2004 | Appel et al. | |
| 2005/0026262 A1 | 2/2005 | Yoshitani et al. | |
| 2005/0173309 A1 | 8/2005 | Bork et al. | |
| 2006/0001187 A1 | 1/2006 | Allen, III et al. | |
| 2006/0118469 A1 | 6/2006 | Bork et al. | |
| 2007/0272597 A1 | 11/2007 | De Feraudy et al. | |
| 2009/0056201 A1 | 3/2009 | Morgan | |
| 2011/0266377 A1 | 11/2011 | Lindner | |
| 2012/0190102 A1 | 7/2012 | Gitschel et al. | |
| 2013/0181076 A1 | 7/2013 | De Feraudy et al. | |
| 2017/0210032 A1 | 7/2017 | Tamir | |
| 2018/0119035 A1 | 5/2018 | Tamir | |

FOREIGN PATENT DOCUMENTS

| | | |
|---|---|---|
| AU | 682825 | 10/1997 |
| CN | 1659007 | 8/2005 |
| DE | 4033701 | 4/1992 |
| DE | 102008056311 | 5/2010 |
| EA | 13190 | 2/2010 |
| EP | 1711323 | 10/2006 |
| JP | 2001-137739 | 5/2001 |
| JP | 2010-228408 | 10/2010 |
| RU | 1055041 | 10/1993 |
| RU | 37633 | 9/1998 |
| RU | 2276012 | 5/2006 |
| WO | WO 03/086733 | 10/2003 |
| WO | WO 2005/077630 | 8/2005 |
| WO | WO 2005/092708 | 10/2005 |
| WO | WO 2006/035441 | 4/2006 |
| WO | WO 2006/079842 | 8/2006 |
| WO | WO 2009/061556 | 5/2009 |
| WO | WO 2010/082202 | 7/2010 |
| WO | WO 2013/006567 | 1/2013 |
| WO | WO 2015/173806 | 11/2015 |
| WO | WO 2015/173807 | 11/2015 |
| WO | WO 2016/181392 | 11/2016 |

OTHER PUBLICATIONS

Welle "Twenty Years of PET Bottle to Bottle Recycling—An Overview", Resources, Conservation and Recycling, 55(11): 865-875, Sep. 2011. Abstract, Sections 3.3-3.8, Figs.5-6, 8.
Communication Pursuant to Rule 164(1) EPC [Supplementary Partial European Search Report and the European Provisional Opinion] dated Jan. 16, 2018 From the European Patent Office Re. Application No. 15792113.1. (17 Pages).
Search Report and Written Opinion dated Aug. 31, 2017 From the Intellectual Property Office of Singapore Re. Application No. 11201609466U. (12 Pages).
Notification of Office Action and Search Report dated May 24, 2018 From the State Intellectual Property Office of the People's Republic of China Re. Application No. 201580036069.2 and Its Translation of Office Action Into English. (8 Pages).
Supplementary European Search Report and the European Search Opinion dated Apr. 20, 2018 From the European Patent Office Re. Application No. 15792113.1. (13 Pages).
Notification of Office Action and Search Report dated Mar. 7, 2018 From the State Intellectual Property Office of the People's Republic of China Re. Application No. 201580037770.6. (7 Pages).
Translation Dated Mar. 21, 2018 of Notification of Office Action dated Mar. 7, 2018 From the State Intellectual Property Office of the People's Republic of China Re. Application No. 201580037770.6. (3 Pages).
Written Opinion dated Jul. 16, 2018 From the Intellectual Property Office of Singapore, IPOS Re. Application No. 11201609461Q. (9 Pages).
Supplementary European Search Report and the European Search Opinion dated Mar. 28, 2018 From the European Patent Office Re. Application No. 15792897.9. (11 Pages).
International Preliminary Report on Patentability dated Nov. 23, 2017 From the International Bureau of WIPO Re. Application. PCT/IL2016/050496. (9 Pages).
Search Report and Written Opinion dated Aug. 17, 2017 From the Intellectual Property Office of Singapore, IPOS Re. Application No. 11201609461Q. (11 Pages).
Keppert et al. "Properties of Concrete With Municipal Solid Waste Incinerator Bootom Ash", 2012 IACSIT Coimbatore Conferences, IPCSIT, 28: 127-131, Feb. 18, 2012. Abstract.
Mussatto et al. "Lignocellulose as Raw Material in Fermentation Processes", Current Research, Technology and Education Topics in Applied Microbiology and Microbial Biotechnology, 2: 897-907, 2010. Abstract.
International Preliminary Report on Patentability dated Nov. 24, 2016 From the International Bureau of WIPO Re. Application No. PCT/IL2015/050492. (9 Pages).
International Preliminary Report on Patentability dated Nov. 24, 2016 From the International Bureau of WIPO Re. Application No. PCT/IL2015/050493. (7 Pages).
International Search Report and the Written Opinion dated Aug. 17, 2015 From the International Searching Authority Re. Application No. PCT/IL2015/050492.

(56) References Cited

OTHER PUBLICATIONS

International Search Report and the Written Opinion dated Aug. 25, 2015 From the International Searching Authority Re. Application No. PCT/IL2015/050493.
International Search Report and the Written Opinion dated Aug. 31, 2016 From the International Searching Authority Re. Application No. PCT/IL2016/050496.
Communication Pursuant to Rule 164(1) EPC [Supplementary Partial European Search Report and the Provisional Opinion] dated Dec. 22, 2017 From the European Patent Office Re. Application No. 15792897.9. (14 Pages).
Communication Pursuant to Article 94(3) EPC dated Dec. 6, 2018 From the European Patent Office Re. Application No. 15792113.1. (5 Pages).
Notification of Office Action and Search Report dated Nov. 15, 2018 From the State Intellectual Property Office of the People's Republic of China Re. Application No. 201580037770.6 and Its Translation of Office Action Into English. (13 Pages).
Cheng et al. "Introduction to Environmental Science", East China University of Science and Technology Press, p. 172, Aug. 2012.
DEFRA "Mechanical Biological Treatment of Municipal solid Waste", Department for Environment Food & Rural Affairs, DEFRA, p. 1-47, Feb. 2013.
Wang et al. "Intelligent Management of Urban Living Garbage", Metallurgical Industry Press, p. 120, Jun. 2009.
Zhuang "Solid Waste Treatment and Disposal", Chemical Industry Press, p. 33, Mar. 2004.
Request for Examination and Search Report dated Dec. 6, 2018 From the Federal Government Institution, Federal Institute of Industrial Property of the Federal Service for Intellectual Property, Patents and Trademarks of the Russian Federation Re. Application No. 2016147997 and Its Translation of Office Action Into English.
Examination Report dated Feb. 8, 2019 From the Australian Government, IP Australia Re. Application No. 2015260783. (4 Pages).

\* cited by examiner

METHOD OF SEPARATING WASTE MATERIAL

RELATED APPLICATIONS

This application is a National Phase of PCT Patent Application No. PCT/IL2015/050493 having International filing date of May 11, 2015, which claims the benefit of priority under 35 USC § 119(e) of U.S. Provisional Patent Application No. 61/991,586 filed on May 11, 2014. The contents of the above applications are all incorporated by reference as if fully set forth herein in their entirety.

FIELD AND BACKGROUND OF THE INVENTION

The present invention, in some embodiments thereof, relates to waste management and, more particularly, but not exclusively, to methods and systems for separating waste material and separated materials produced thereby.

The most common method of disposing of waste material is deposition in landfills. However, environmental concerns and/or the cost of land may render this method unsatisfactory.

Standard recycling of waste material typically requires sorting of waste material into different types of material, and recycling or discarding the different types of material separately.

An alternative to standard recycling is production of refuse-derived fuel (RDF) by shredding and dehydrating solid waste material, and combustion of the RDF in power plants.

U.S. Pat. No. 6,017,475 describes a process of converting household garbage into useful byproducts by reducing the garbage to an aggregate shard, optionally expelling liquid from the aggregate shard, and heating the aggregate shard under pressure to create a pulp. A system comprising a grinder for converting household garbage to an aggregate shard, and a hydrolyzer for decomposing the remaining aggregate shard after the liquid has been removed, to form the pulp, is also described. The process hydrolyzes lignocellulose in the garbage, to obtain an aggregate cellulose pulp having traces of metals and plastics. As further described therein, the aggregate cellulose pulp can be separated into pure cellulose pulp and a residue containing inorganic materials.

U.S. Pat. No. 7,497,335 describes "hydrogravity" separation of a multiple domain solid feedstock to produce particles of each substantially a single domain, each type of particle having a different density. Particles are slurried into a suitable fluid to effect binary separation of the mixture of particles into a stream with a higher average specific gravity and a stream with a lower average specific gravity.

U.S. Pat. No. 6,368,500 describes a system for treatment of collected waste, the system comprising at least one separator for separating between first waste material having a specific gravity equal to or less than that of water and second waste material having a specific gravity above that of water; at least one crusher for producing a liquid product from the first waste material; and acetogenic and methanogenic fermentors for fermenting the liquid product.

International Patent Application having Publication No. WO 2006/035441 describes a method of encapsulating pieces of waste with melted plastic by heating and mixing.

International Patent Application having Publication No. WO 2010/082202 describes a composite material prepared by drying waste, and heating the dried waste while mixing under shear forces. The composite material has thermoplastic properties, and is processed to obtain useful articles.

Additional background art includes International Patent Applications having Publication Nos. WO 2005/077630, WO 2005/092708 and WO 2006/079842; European Patent No. 1711323; KR 2003/0014929; U.S. Pat. Nos. 3,850,771, 4,013,616, 4,772,430, 4,968,463, 5,217,655, 6,017,475, 6,253,527 and 6,423,254; and U.S. patent applications having Publication Nos. 2004/0080072 and 2004/0080072.

SUMMARY OF THE INVENTION

According to an aspect of some embodiments of the invention, there is provided a method of separating waste material, the method comprising subjecting the waste material to a separation process according to specific gravity, so as to obtain at least two fractions, the fractions comprising at least a first fraction which comprises a low-density material and a second fraction which comprises a high-density material, thereby separating the waste material to a plurality of separated materials.

According to an aspect of some embodiments of the invention, there is provided a polymeric material, obtainable according to a method described herein.

According to an aspect of some embodiments of the invention, there is provided a compost, obtainable according to a method described herein.

According to an aspect of some embodiments of the invention, there is provided a concrete, obtainable according to a method described herein.

According to an aspect of some embodiments of the invention, there is provided a system for separating a waste material, the system comprising:

at least one separator configured for separating materials in the waste material according to specific gravity so as to obtain at least two fractions, the fractions comprising at least a first fraction which comprises a low density material and at least a second fraction which comprises a high-density material, the separator containing an aqueous liquid selected such that a portion of the waste material sinks and another portion does not sink, thereby obtaining the first fraction and the second fraction.

According to an aspect of some embodiments of the invention, there is provided a method of processing waste material, the method comprising:

separating materials in the waste material according to specific gravity, the separating comprising contacting the waste material with an aqueous liquid selected such that a portion of said waste material sinks, thereby obtaining material which sinks and material which does not sink, and
at least one of:
i) subjecting at least a portion of the material which does not sink to a fermentation process, thereby obtaining at least one fermentation product and an organic residue;
ii) heating at least a portion of the material which does not sink, thereby obtaining a processed polymeric material;
iii) separating oils from the material which does not sink, and preparing a fuel from the oils; and
iv) separating metal from the material which sinks, thereby obtaining a separated metal, and/or preparing a concrete comprising at least a portion of the material which sinks as an aggregate,
thereby processing waste material.

According to some embodiments of the invention, the plurality of separated materials comprises at least two materials selected from a low-density polymeric material, a high-density polymeric material, a metal, a glass, an oil, and lignocellulose.

According to some embodiments of the invention, the method further comprises processing at least one of the separated materials to thereby obtain at least one processed material selected from a processed polymeric material, a compost, a biogas, ethanol, a biodiesel fuel and a concrete.

According to some embodiments of the invention, the separation process comprises contacting the waste material with an aqueous liquid selected such that a portion of the waste material sinks and another portion does not sink, thereby obtaining the first fraction comprising a low density material and the second fraction comprising a high-density material.

According to some embodiments of the invention, a specific gravity of the aqueous liquid is at least 1.05.

According to some embodiments of the invention, the separation process comprises contacting the waste material with a first aqueous liquid selected such that a portion of the waste material sinks, thereby obtaining the second fraction comprising a high-density material and the first fraction comprising a low-density material, and further contacting at least one of the first fraction and the second fraction with a second aqueous liquid selected such that a portion of the fraction sinks, thereby obtaining a third fraction comprising a low-density material which does not sink in either of the aqueous liquids, a fourth fraction comprising an intermediate-density material which sinks in one of the aqueous liquids, and a fifth fraction comprising a high-density material which sinks in both of the aqueous liquids.

According to some embodiments of the invention, a specific gravity of one of the first aqueous liquid and the second aqueous liquid is at least 1.05, and a specific gravity of the other of the first aqueous liquid and the second aqueous liquid is no more than 1.01.

According to some embodiments of the invention, the intermediate-density material comprises a separated lignocellulose.

According to some embodiments of the invention, the low-density material in the third fraction comprises a separated low-density polymeric material.

According to some embodiments of the invention, the low-density polymeric material comprises at least 50 weight percents polyolefins by dry weight.

According to some embodiments of the invention, the method further comprises subjecting at least a portion of the first fraction which comprises a low-density material to a fermentation process.

According to some embodiments of the invention, the method further comprises subjecting at least a portion of the fourth fraction which comprises an intermediate-density material to a fermentation process.

According to some embodiments of the invention, the fermentation process produces a biogas and/or ethanol.

According to some embodiments of the invention, the method further comprises processing at least a portion of an organic residue remaining after the fermentation process to thereby obtain a compost.

According to some embodiments of the invention, the method further comprises separating oil from a fraction which comprises a low-density material, to thereby obtain a separated oil.

According to some embodiments of the invention, separating the oil comprises skimming the oil off of a surface of an aqueous liquid contacted with the waste material.

According to some embodiments of the invention, the method further comprises processing the oil to thereby obtain a biodiesel fuel.

According to some embodiments of the invention, the high-density material comprises at least one of a metal and a high-density non-metallic material, and the method further comprises separating the high-density material to thereby obtain a separated metal and/or a separated high-density non-metallic material.

According to some embodiments of the invention, the high-density non-metallic material comprises at least one of a glass and a high-density polymeric material, and the method further comprises separating the high-density non-metallic material, to thereby obtain a separated glass and/or a separated high-density polymeric material.

According to some embodiments of the invention, the method further comprises contacting an aggregate comprising the high-density non-metallic material with a binder to thereby form a concrete.

According to some embodiments of the invention, the concrete is a polymer concrete.

According to some embodiments of the invention, the method further comprises processing a low-density material separated from the waste material to thereby obtain a processed polymeric material.

According to some embodiments of the invention, the processing comprises heating a feedstock comprising the low density material.

According to some embodiments of the invention, the low-density material comprises a separated low-density material in one or more of the first fraction and the third fraction.

According to some embodiments of the invention, the low-density material is processed together with an organic residue remaining after a fermentation process.

According to some embodiments of the invention, the waste material is a shredded waste material.

According to some embodiments of the invention, the method further comprises shredding the waste material prior to contacting the waste material with the aqueous liquid.

According to some embodiments of the invention, the method further comprises shredding at least a portion of the first fraction subsequent to contacting the waste material with the aqueous liquid.

According to some embodiments of the invention, the aqueous liquid comprises an aqueous salt solution.

According to some embodiments of the invention, the salt is sodium chloride.

According to some embodiments of the invention, a concentration of the salt in the aqueous salt solution is at least 10 weight percents.

According to some embodiments of the invention, the system further comprises at least one apparatus configured for obtaining at least two materials selected from a low-density polymeric material, a high-density polymeric material, a metal, a glass, an oil, and lignocellulose.

According to some embodiments of the invention, the system further comprises at least one apparatus configured for processing at least a portion of the first fraction or the second fraction to thereby obtain at least one processed material selected from a processed polymeric material, a compost, a biogas, ethanol, a biodiesel fuel and a concrete.

According to some embodiments of the invention, the at least one separator comprises a first separator containing a first aqueous liquid and a second separator containing a second aqueous liquid, the first separator and the second separator being in communication, and the second separator being configured for receiving at least one fraction from the first separator, and for separating the fraction received from the first separator according to specific gravity, the second aqueous liquid being selected such that a portion of the fraction received from the first separator sinks, thereby obtaining a third fraction comprising a low-density material which does not sink in either of the aqueous liquids, a fourth fraction comprising an intermediate-density material which sinks in one of the aqueous liquids, and a fifth fraction comprising a low-density material which sinks in both of the aqueous liquids.

According to some embodiments of the invention, the second separator is configured for obtaining a separated lignocellulose, the intermediate-density material comprising the lignocellulose.

According to some embodiments of the invention, the second separator is configured for obtaining a separated low-density polymeric material, the low-density material in the third fraction comprising the low-density polymeric material.

According to some embodiments of the invention, the system further comprises a bioreactor in communication with at least one of the at least one separator, the bioreactor being configured for subjecting at least a portion of the first fraction which comprises a low-density material to a fermentation process.

According to some embodiments of the invention, the system further comprises a bioreactor in communication with the second separator, the bioreactor being configured for subjecting at least a portion of the fourth fraction which comprises an intermediate-density material to a fermentation process.

According to some embodiments of the invention, the bioreactor is configured for obtaining a biogas and/or ethanol.

According to some embodiments of the invention, the system comprises an apparatus configured for collecting an organic residue in the bioreactor and processing collected organic residue to thereby obtain a compost.

According to some embodiments of the invention, the system comprises an oil-water separator configured for separating oil from a fraction which comprises a low-density material, to thereby obtain a separated oil.

According to some embodiments of the invention, the oil-water separator comprises a skimmer.

According to some embodiments of the invention, the system further comprises a subsystem configured for processing the oils to thereby obtain a biodiesel fuel.

According to some embodiments of the invention, the system comprises an apparatus in communication with the separator, the apparatus being configured for receiving the high-density material from the separator, wherein the high-density material comprises at least one of a metal and a high-density non-metallic material, and for separating the high-density material, to thereby obtain a separated metal and/or a separated high-density non-metallic material.

According to some embodiments of the invention, the system further comprises at least one apparatus configured for separating the high-density non-metallic material, wherein the high-density non-metallic material comprises at least one of a glass and a high-density polymeric material, to thereby obtain a separated glass and/or a separated high-density polymeric material.

According to some embodiments of the invention, the system further comprises a subsystem configured for grinding at least a portion of the high-density non-metallic material into an aggregate and preparing a concrete from the aggregate.

According to some embodiments of the invention, the system further comprises an apparatus configured for preparing a feedstock which comprises at least a portion of the low-density material in the third fraction and at least a portion of an organic residue in the bioreactor.

According to some embodiments of the invention, the system comprises an apparatus configured for processing a low-density material separated from the waste material, to thereby obtaining a processed polymeric material.

According to some embodiments of the invention, the system further comprises a shredder configured for shredding at least a portion of the first fraction subsequent to contacting the waste material with the aqueous liquid.

According to some embodiments of the invention, the system further comprises a monitor for monitoring a specific gravity of the aqueous liquid in the separator, wherein the system is configured to adjust a specific gravity of the aqueous liquid in the separator to a predetermined value.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

DESCRIPTION OF SPECIFIC EMBODIMENTS OF THE INVENTION

Figure 1:
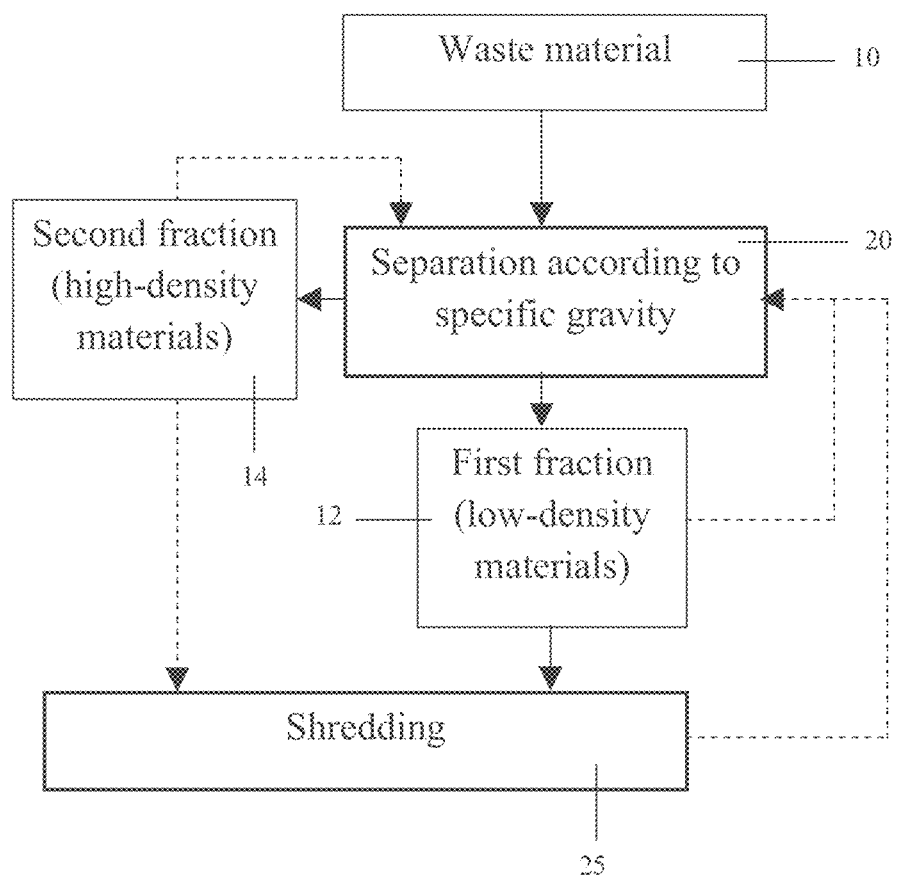
FIG. 1 is a flow chart depicting a method of separating waste material according to specific gravity, according to some embodiments of the invention.

The present invention, in some embodiments thereof, relates to waste management and, more particularly, but not exclusively, to methods and systems for separating waste material and separated materials produced thereby.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

The present inventor has uncovered a separation process that can be used to obtain, in an efficient and cost-effective manner, a plurality of separated materials useful as is and/or as raw materials suitable for further processing. For example, contacting waste materials (e.g., unsorted waste materials) with a liquid such as an aqueous solution can be utilized to advantageously separate waste material according to specific gravity into at least two fractions, wherein the obtained fractions are or contain separated materials which are useful per se and/or can be further separated and/or processed into useful separated materials. Furthermore, the properties of the obtained separated materials are controllable, for example, by adjusting a specific gravity of one or more liquids used to separate waste material according to specific gravity.

Referring now to the drawings, FIG. 1 illustrates a general procedure for separating waste material according to specific gravity, according to exemplary embodiments of the invention, as described in detail in the Examples section that follows.

Figure 2:
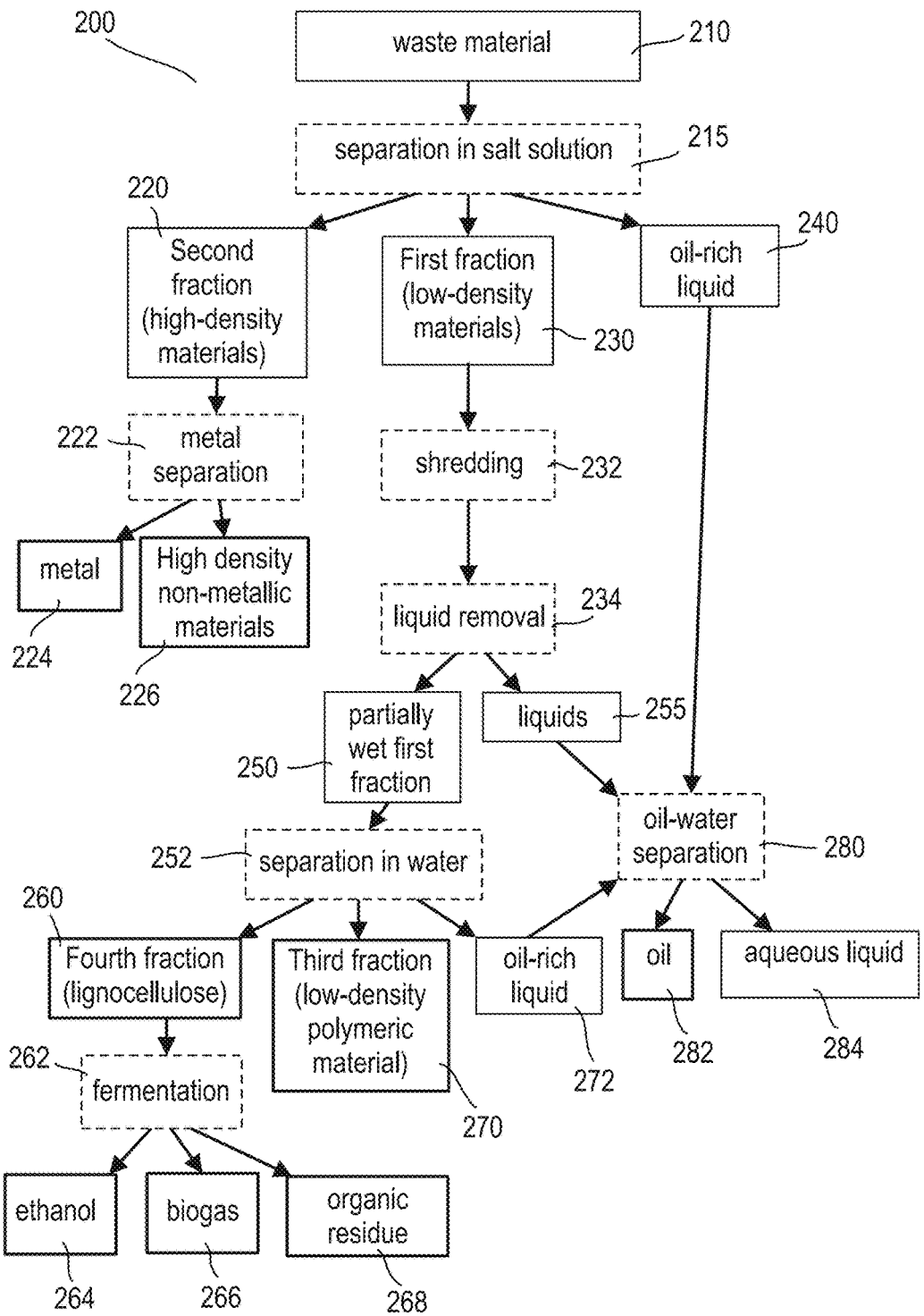
FIG. 2 is a flow chart depicting a method of separating waste material, according to some embodiments of the invention.

FIG. 2 illustrates a general procedure for separating waste material into a plurality of separated materials, according to exemplary embodiments of the invention, as described in detail in the Examples section that follows.

Figure 3:
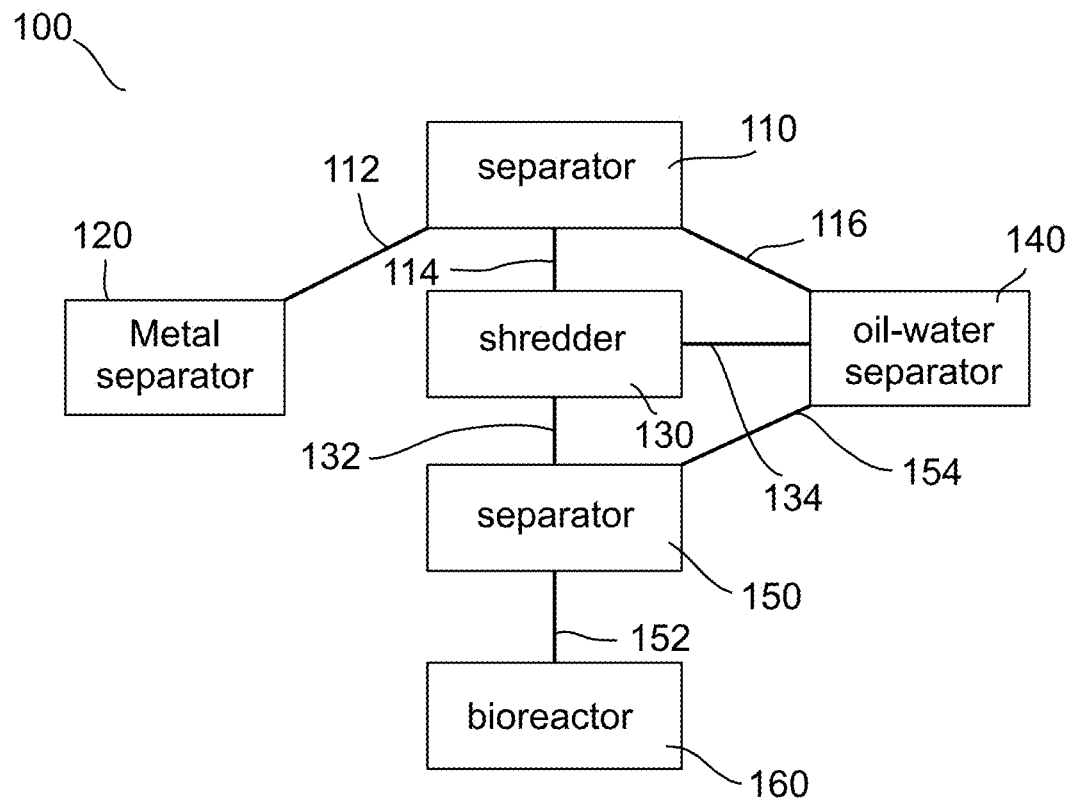
FIG. 3 is a scheme depicting a system for separating waste material according to some embodiments of the invention.
Figure 4:
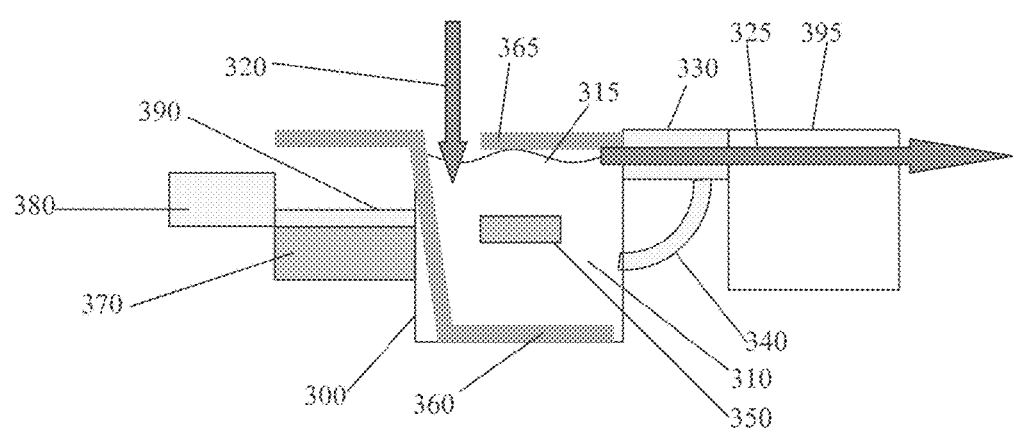
FIG. 4 is a scheme depicting a system for separating waste material according to some embodiments of the invention.

FIG. 3 illustrates a system for separating waste material according to exemplary embodiments of the invention, as described in detail herein under. FIG. 4 illustrates a system for separating waste material according to specific gravity, according to exemplary embodiments of the invention, as described in detail herein under.

Figure 5A:
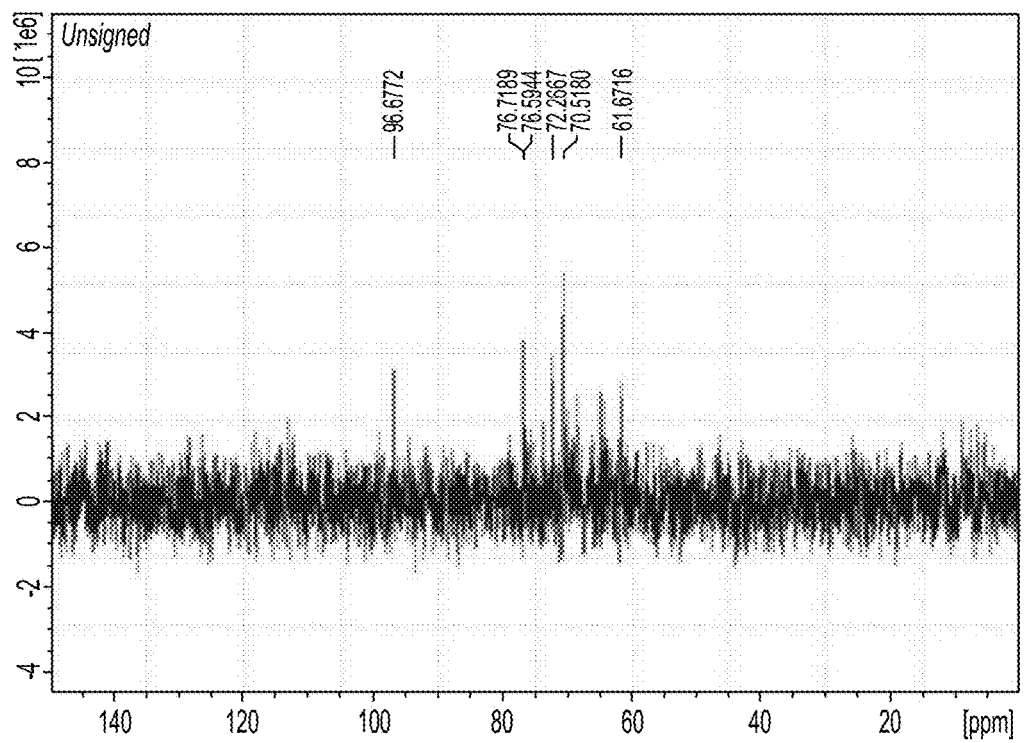
FIGS. 5A and 5B show NMR spectra of a filtrate of sea salt aqueous solution (about 20 weight percents) (FIG. 5A) and fresh water (FIG. 5B), each filtrate being obtained after 3 hours incubation with plant biomass.
Figure 5B:
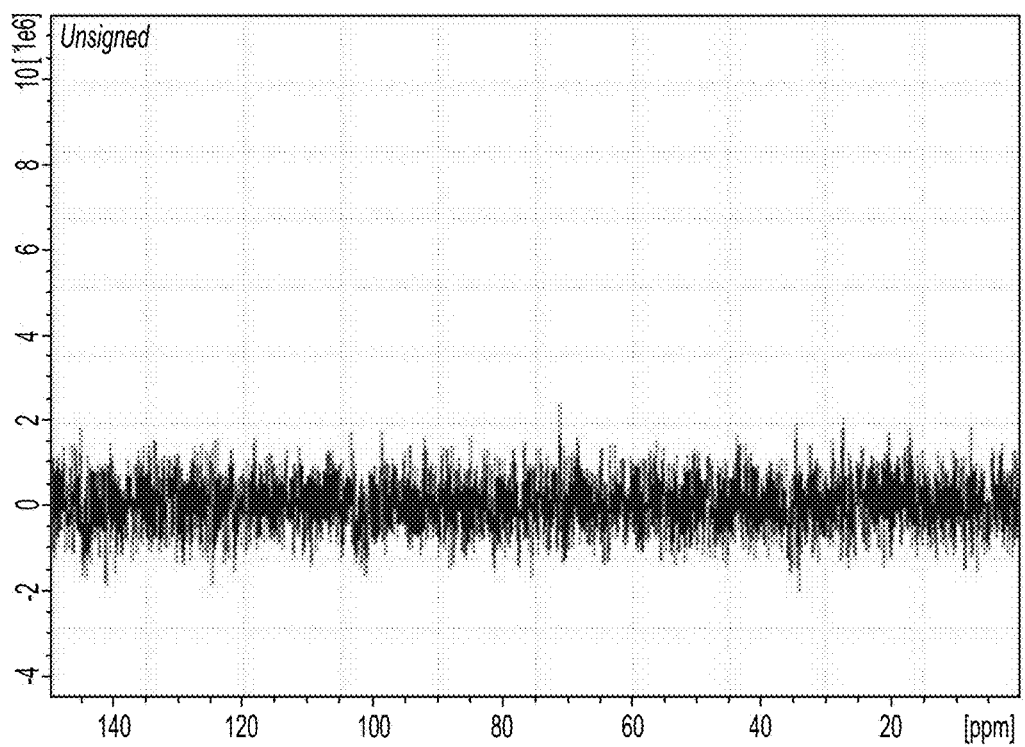

FIGS. 5A and 5B show that hypertonic solution facilitates release of carbohydrates from biomass.

According to an aspect of some embodiments of the present invention, there is provided a method of separating waste material, to thereby obtain a plurality of separated materials. In some embodiments of any of the embodiments described herein, at least two separated materials are obtained. In some embodiments of any of the embodiments described herein, at least three separated materials are obtained. In some embodiments, at least four separated materials are obtained. In some embodiments, at least five separated materials are obtained.

The term "plurality" encompasses two or more materials, that is 2, 3, 4, 5, 6, 7, 8, 9, 10 or more materials.

Examples of separated materials obtainable according to embodiments of the invention include, without limitation, a low-density polymeric material, a high-density polymeric material, a metal, a glass, an oil and lignocellulose. In some embodiments of any of the embodiments described herein, at least two of the aforementioned separated materials are obtained. In some embodiments, at least three of the aforementioned separated materials are obtained. In some embodiments, at least four of the aforementioned separated materials are obtained. In some embodiments, at least five of the aforementioned separated materials are obtained. In some embodiments, all of the aforementioned separated materials are obtained.

Herein throughout, the phrase "separated material" is used to describe a material or a family of materials having similar chemical properties, obtained by removing a portion of materials in a source material (e.g., a waste material) so as to obtain a material having a different composition than the source material, and enriched in a particular material and/or family of materials in comparison with the source material. By "source material" it is meant, for example, the waste material as described herein, which is subjected to the separation as described herein.

By "enriched" it is meant that a concentration of a substance which is enriched is at least 50% greater than in the source material, optionally at least 100% greater (two-fold), optionally at least three-fold, optionally at least five-fold, and optionally at least ten-fold.

A separated material may optionally comprise a mixture of materials of similar chemical properties (a family of materials), e.g., a separated material which is a "polymeric material" encompasses mixtures of polymers, a separated material which is "oil" encompasses mixtures of oils, a separated material which is a "metal" encompasses mixtures of metals, and so forth.

A separated material may also optionally comprise impurities, e.g., a separated material which is a "polymeric material" optionally comprises (in part) non-polymeric substances, a separated material which is "oil" optionally comprises (in part) substances other than oils, a separated material which is a "lignocellulose" optionally comprises (in part) substances other than lignocellulose, and so forth.

Herein "polymeric material" (including the phrases low-density polymeric material" and "high-density polymeric material") refers to a material in which a concentration of respective polymers is at least 50 weight percents of the material by dry weight. The polymers may be synthetic polymers or polymers derived from biomass (e.g., plant material and animal material).

Herein throughout, the term "separating" and grammatical derivations thereof is used to describe a process of obtaining a separated material, as defined herein, from a source material (e.g., a waste material), as defined herein.

Herein, "animal material" refers to material which originates from an animal, and "plant material" refers to material which originates from a plant or fungus. It is noted that coal and petroleum products and the like, which originate from organisms which lived only in the distant past, are not considered herein as animal or plant material.

In some embodiments, the method according to this aspect of the present invention is effected by subjecting the waste material to a separation process according to specific gravity, so as to obtain at least two fractions. In some embodiments, at least one of the fractions, herein referred to as "a first fraction", comprises one or more low-density materials and at least one of the fractions, herein referred to as "a second fraction" comprises one or more high-density materials. Herein, low-density materials indicate lower specific gravity values than high-density materials, the term "density" being used instead of "specific gravity" merely for brevity and to enhance readability.

Thus, the waste material may optionally be in the form it is received at a solid waste management facility or at a waste dump or from a landfill (referred to as "unsorted" waste material), or alternatively, waste material which has undergone preliminary sorting or separation, that is, waste material (e.g., from the aforementioned sources) from which one or more components (e.g., magnetic materials) are selectively removed (partially or entirely) before being separated according to the method described herein. The waste material may include some waste from non-domestic sources, such as sludge (e.g., sewage sludge), industrial waste (e.g., discarded packaging material) and/or agricultural waste.

The waste material typically comprises some liquid (e.g., water, oils), for example, liquids absorbed by the waste material and/or within containers, plant material and/or animal material in the waste material. It is to be appreciated that the method of separating described herein is optionally effected by contact with a liquid, so that the waste material can therefore optionally be separated without any need for prior drying of the waste material.

The Waste Material:

Herein throughout, the phrase "waste material" refers to substantially solid waste, such as municipal solid waste, which, in some embodiments, is obtained mostly from domestic sources (household waste), and is also referred to as "trash" or "garbage". The phrase "waste material" as used herein encompasses substantially unsorted waste material (e.g., prior to removal of a portion of the materials as described herein), that is, it comprises a wide variety of substances typical of domestic waste, and optionally further encompasses waste material, as defined herein, which has undergone some separation (e.g., removal of readily recyclable items).

Some or all of the obtained separated materials according to any of the embodiments described herein may have commercial value (e.g., as a commodity).

Additionally or alternatively, the method further comprises processing one or more of the obtained separated materials (according to any of the embodiments described herein), to thereby obtain a processed material, for example, a processed material with a commercial value that the separated material from which it is derived does not have.

Herein throughout, the term "processing" and grammatical derivations thereof, in the context of an act performed on a material (e.g., a separated material), is used to describe alteration of the composition, chemical properties and/or physical properties of the material, to thereby obtain a different, second material, referred to herein as "processed material", having a different composition, chemical properties and/or physical properties than the material subjected to processing.

For the sake of clarity, the terms "processing" and "processed material" are used herein to describe a material obtained by procedures other than separating, for example, by subjecting a separated material (as defined herein) to one or more chemical reactions and/or combining a separated material with one or more additional materials.

Examples of processed materials which may be obtained by some embodiments of the invention include, without limitation, a processed polymeric material (which may optionally be obtained by processing a separated polymeric material); a compost, a biogas and/or ethanol (which may optionally be obtained by processing separated lignocellulose); a biofuel (which may optionally be obtained by processing a separated oil); and/or a concrete (which may optionally be obtained by processing high-density materials). Such processing is described in more detail hereinbelow.

Separation Process Utilizing Liquid:

As used herein, the term "specific gravity" refers to a ratio of density of a material to a density of pure water under the same conditions (e.g., temperature, pressure). Thus, the specific gravity of pure water is defined as 1. In some embodiments of any of the embodiments described herein, the specific gravity is a specific gravity at room temperature (e.g., 25° C.) and atmospheric pressure. However, because specific gravity is a ratio, it is less sensitive than density to changes in conditions (e.g., temperature, pressure). Hence, in some embodiments of any of the embodiments described herein, the specific gravity is a specific gravity under working conditions. For example, ambient temperature under working conditions may vary, for example, within a range of 0° C. to 50° C., and ambient pressure may vary according to altitude of the location.

In some embodiments of any of the embodiments described herein, the separation process comprises contacting the waste material with a liquid selected such that a portion of the waste material sinks in the liquid and another portion does not sink.

The liquid may be any type of liquid, including a pure liquid, a solution, and a suspension. In some embodiments of any of the embodiments described herein, the liquid is an aqueous liquid.

In embodiments utilizing a liquid, a fraction of low-density materials (referred to herein as a "first fraction"), comprising materials which do not sink, is obtained; and a fraction of high-density materials (referred to herein as a "second fraction"), comprising materials which sink, is obtained. At least one of the first and second fractions may be collected and optionally separated further, in order to obtain a separated material according to any of the embodiments described herein.

Herein, the term "sink" encompasses sinking to a bottom of a liquid (e.g., sedimenting), as well as sinking below a surface of the liquid.

In some of any of the embodiments described herein, to "sink" refers to sinking to a bottom of a liquid (e.g., sedimenting), such that materials which sink below a surface of the liquid but do not sink to a bottom of the liquid are considered as materials which do not sink, and are optionally included in a fraction of low-density materials (e.g., a first fraction) according to any of the respective embodiments described.

In some of any of the embodiments described herein, to "sink" refers to sinking below a surface of a liquid, such that materials which sink below a surface of the liquid but do not sink to a bottom of the liquid are considered as materials sink, and are optionally included in a fraction of high-density materials (e.g., a second fraction) according to any of the respective embodiments described.

In some of any of the embodiments described herein, materials which sink below a surface of the liquid but do not sink to a bottom of the liquid are not included in either a fraction of low-density materials (e.g., a first fraction) or a fraction of high-density materials (e.g., a second fraction) according to any of the respective embodiments described.

In some of any of the embodiments described herein, at least a portion of the inorganic materials of a waste material (which are frequently denser than organic materials) sink to a bottom of the liquid.

In some of any of the embodiments described herein, materials which sink to the bottom are removed (e.g., by removing sediment), and substantially all other materials are collected as a first fraction according to any of the respective embodiments described herein.

In some of any of the embodiments described herein, the separation process comprises removing substantially all of the material from the liquid (e.g., both the fraction of low-density materials and the fraction of high-density materials), such that the liquid can be reused to separate more waste material according to specific gravity. Removal from the liquid can be for example, by skimming floating material from a surface, removing sedimented material, and/or filtering out material which sinks below a surface of the liquid but does not sink to the bottom.

The specific gravity of the liquid may be selected in accordance with the materials which are desired to be included within a fraction of low-density materials (e.g., first fraction) and/or with the materials which are desired to be included within a fraction of high-density materials (e.g., second fraction).

Without being bound by any particular theory, it is believed that that separation by contacting waste material with a liquid may be readily performed using wet waste material (e.g., waste material that has not been dried), whereas wet waste material may pose an obstacle to other separation techniques, for example, by resulting in fragments of different types of material sticking to one another.

In some embodiments of any of the embodiments relating to utilization of a liquid, at least two distinct liquids are utilized, and at least three fractions are obtained.

In some embodiments, the separation process comprises contacting the waste material with a first aqueous liquid, to thereby obtain a first and second fraction as described herein, and further comprises contacting at least one (optionally only one) of the first fraction and the second fraction with a second aqueous liquid, thereby obtaining a third fraction of low-density materials which do not sink in either of the first or second aqueous liquids, a fourth fraction of intermediate-density materials which sink in one of the aqueous liquids (e.g., whichever liquid has a lower specific gravity), and a fifth fraction of high-density materials which sink in both the first and second aqueous liquids.

The second aqueous liquid is selected such that a portion of the fraction contacted therewith sinks. In some embodiment of any of the embodiments relating to a first and second aqueous liquid, the second aqueous liquid has a different specific gravity than the first aqueous liquid.

In some embodiment of any of the embodiments relating to a first and second aqueous liquid, specific gravities of the first and second aqueous liquids differ by at least 0.01. In some embodiments, specific gravities of the first and second aqueous liquids differ by at least 0.02. In some embodiments, specific gravities of the first and second aqueous liquids differ by at least 0.03. In some embodiments, specific gravities of the first and second aqueous liquids differ by at least 0.05. In some embodiments, specific gravities of the first and second aqueous liquids differ by at least 0.07. In some embodiments, specific gravities of the first and second aqueous liquids differ by at least 0.1. In some embodiments, specific gravities of the first and second aqueous liquids differ by at least 0.15. In some embodiments, specific gravities of the first and second aqueous liquid differ by at least 0.2.

Herein, the phrases "materials which do not sink in either of the first or second aqueous liquids", "materials which do not sink in either of said aqueous liquids" and the like, encompass materials which do not sink in whichever of the aqueous liquids has the lowest specific gravity, without requiring any determination of the behavior of the materials in a liquid with a higher specific gravity.

Similarly, herein, the phrase "materials which sink in both the first and second aqueous liquids", "materials which sink in both of said aqueous liquids" and the like, encompass materials which sink in whichever of the aqueous liquids has the highest specific gravity, without requiring any determination of the behavior of the materials in a liquid with a lower specific gravity.

It is to be understood that the phrases "third fraction", "fourth fraction" and "fifth fraction" merely indicate that the separation process comprises at least two separations which result in at least three fractions, and does not necessarily mean that the fraction is different than a "first fraction" or "second fraction" described herein.

It is also to be understood that the phrases "first fraction" and "second fraction" indicate that those two fractions are obtained during the separation process, and does not necessarily mean that the separation process does not comprise further separation into three or more fractions, as described herein. Such further separation may be before and/or after the separation into first and second fractions.

In some embodiment of any of the embodiments described herein, a first fraction of low-density materials obtained using a first aqueous liquid is contacted with a second aqueous liquid, wherein the second aqueous liquid has a lower specific gravity than the first aqueous liquid. In some such embodiments, the second fraction of high-density materials is identical to the fifth fraction of high-density materials, and the first fraction of low-density materials is separated into the third fraction of low-density materials and the fourth fraction of intermediate-density materials. It is to be appreciated that in such embodiments, the fourth fraction may be considered the fraction of high-density materials with respect to the second aqueous liquid.

In some embodiment of any of the embodiments described herein, a second fraction of high-density materials obtained using a first aqueous liquid is contacted with a second aqueous liquid, wherein the second aqueous liquid has a higher specific gravity than the first aqueous liquid. In some such embodiments, the first fraction of low-density materials is identical to the third fraction of low-density materials, and the second fraction of high-density materials is separated into the fifth fraction of high-density materials and the fourth fraction of intermediate-density materials. It is to be appreciated that in such embodiments, the fourth fraction of intermediate-density materials may be considered the fraction of low-density materials with respect to the second aqueous liquid.

In some embodiment of any of the embodiments described herein relating to two aqueous liquids having different specific gravities, use of the liquid with a higher specific gravity as the first aqueous liquid and use of the liquid with a higher specific gravity as the second aqueous liquid result in substantially the same fractions, that is the fractions are not substantially affected by the order in which the liquids are utilized.

In some embodiment of any of the embodiments described herein relating to two aqueous liquids having different specific gravities, a specific gravity of one of the aqueous liquids is no more than 1.01, the liquid optionally being water. In some such embodiments, a specific gravity of the other of the two aqueous liquids is at least 1.03 (e.g., according to any of the embodiments described herein relating to a liquid with such a specific gravity). In some such embodiments, a specific gravity of the other of the two aqueous liquids is at least 1.05 (e.g., according to any of the embodiments described herein relating to a liquid with such a specific gravity). In some such embodiments, a specific gravity of the other of the two aqueous liquids is at least 1.07 (e.g., according to any of the embodiments described herein relating to a liquid with such a specific gravity). In some such embodiments, a specific gravity of the other of the two aqueous liquids is at least 1.10 (e.g., according to any of the embodiments described herein relating to a liquid with such a specific gravity). In some such embodiments, a specific gravity of the other of the two aqueous liquids is at least 1.15 (e.g., according to any of the embodiments described herein relating to a liquid with such a specific gravity). In some such embodiments, a specific gravity of the other of the two aqueous liquids is at least 1.20 (e.g., according to any of the embodiments described herein relating to a liquid with such a specific gravity).

In some embodiment of any of the embodiments described herein relating to two aqueous liquids having different specific gravities, a specific gravity of one of the aqueous liquids is no more than 1.00, the liquid optionally being water. In some such embodiments, a specific gravity of the other of the two aqueous liquids is at least 1.03 (e.g., according to any of the embodiments described herein relating to a liquid with such a specific gravity). In some such embodiments, a specific gravity of the other of the two aqueous liquids is at least 1.05 (e.g., according to any of the embodiments described herein relating to a liquid with such a specific gravity). In some such embodiments, a specific gravity of the other of the two aqueous liquids is at least 1.07 (e.g., according to any of the embodiments described herein relating to a liquid with such a specific gravity). In some such embodiments, a specific gravity of the other of the two aqueous liquids is at least 1.10 (e.g., according to any of the embodiments described herein relating to a liquid with such a specific gravity). In some such embodiments, a specific gravity of the other of the two aqueous liquids is at least 1.15 (e.g., according to any of the embodiments described herein relating to a liquid with such a specific gravity). In some such embodiments, a specific gravity of the other of the two aqueous liquids is at least 1.20 (e.g., according to any of the embodiments described herein relating to a liquid with such a specific gravity).

In some embodiment of any of the embodiments described herein relating to two aqueous liquids having different specific gravities, the aqueous liquid having a higher specific gravity is an aqueous salt solution according to any of the respective embodiments described herein.

In some embodiments of any of the embodiments described herein, the method provides at least one fraction enriched in material having a specific gravity within a pre-selected range, and the liquid is selected in accordance with the pre-selected range (e.g., selection of a suitable concentration for an aqueous salt solution, as discussed in further detail herein).

In some embodiments of any of the embodiments described herein, the fraction(s) contains at least 90 weight percents of material having a specific gravity within a pre-selected range. In some embodiments, the fraction(s) contains at least 95 weight percents of material having a specific gravity within a pre-selected range. In some embodiments, the fraction(s) contains at least 98 weight percents of material having a specific gravity within a pre-selected range. In some embodiments, the fraction(s) contains at least 99 weight percents of material having a specific gravity within a pre-selected range. Any value between 90 and 99.9 weight percents is also contemplated according to these embodiments.

A pre-selected range for the specific gravity may optionally be characterized by an upper limit and a lower limit, or alternatively, the range may optionally be an open-ended range, for example, characterized by an upper limit with no lower limit, or by a lower limit with no upper limit.

In some embodiments of any of the embodiments described herein, the pre-selected range for a first fraction of low-density materials according to any of the respective embodiments described herein is no more than 1.25, that is, the upper limit of the pre-selected range is no more than 1.25, such that the entire range is no more than 1.25. In some embodiments, the pre-selected range is no more than 1.225. In some embodiments, the pre-selected range is no more than 1.20. In some embodiments, the pre-selected range is no more than 1.175. In some embodiments, the pre-selected range is no more than 1.15. In some embodiments, the pre-selected range is no more than 1.125. In some embodiments, the pre-selected range is no more than 1.10. In some embodiments, the pre-selected range is no more than 1.075. In some embodiments, the pre-selected range is no more than 1.05. In some embodiments, the pre-selected range is no more than 1.025. In some embodiments, the pre-selected range is no more than 1.00.

In some embodiments of any of the embodiments described herein, the pre-selected range for a third fraction of low-density materials according to any of the respective embodiments described herein is no more than 1.25, that is, the upper limit of the pre-selected range is no more than 1.25, such that the entire range is no more than 1.25. In some embodiments, the pre-selected range is no more than 1.225. In some embodiments, the pre-selected range is no more than 1.20. In some embodiments, the pre-selected range is no more than 1.175. In some embodiments, the pre-selected range is no more than 1.15. In some embodiments, the pre-selected range is no more than 1.125. In some embodiments, the pre-selected range is no more than 1.10. In some embodiments, the pre-selected range is no more than 1.075. In some embodiments, the pre-selected range is no more than 1.05. In some embodiments, the pre-selected range is no more than 1.025. In some embodiments, the pre-selected range is no more than 1.00.

In some of any of the embodiments described herein, the waste material is stirred in the liquid, for example, by rotation of at least one paddle (e.g., rotation of a paddle wheel). Stirring is optionally selected to be sufficiently vigorous to facilitate separation of different types of material (which may be stuck to one another, for example), while being sufficiently gentle to allow separation of materials in the liquid.

In some of any of the embodiments described herein, the stirring comprises perturbation (e.g., rotation, vibration, agitation) at a frequency of 120 per minute or less. In some embodiments, stirring comprises perturbation at a frequency of 60 per minute or less. In some embodiments, stirring comprises perturbation at a frequency of 30 per minute or less. In some embodiments, stirring comprises perturbation at a frequency of 20 per minute or less. In some embodiments, stirring comprises perturbation at a frequency of 10 per minute or less.

Although embodiments comprising one or two cycles of separating materials according to specific gravity are described herein explicitly, it is to be understood that in some of any of the embodiments described herein, the method comprises more than two cycles of separating materials according to specific gravity.

In addition, it is to be understood that each cycle may be effected with a liquid (e.g., an aqueous salt solution) which is the same or different than a liquid (e.g., an aqueous salt solution) used in another cycle, and that each cycle may independently comprise separating a fraction of high-density materials (e.g., materials which sink in the liquid) and/or removing a fraction of low-density materials (e.g., materials which float in the liquid).

In some of any of the embodiments described herein, removal of liquid from a fraction is performed subsequent to at least one cycle of separating materials according to specific gravity. The removal of liquid may optionally be effected by drainage (e.g., gravity-driven drainage) and/or compression of the separated material, for example, using a screw press. Optionally, at least a portion of the removed liquid is reused for separating materials as described herein.

In some of any of the embodiments described herein, removed liquid comprises liquid which originates in the waste material, for example, aqueous liquids and/or oils. For example, liquid removed according to any of the respective embodiments described herein (e.g., by drainage and/or compression) may optionally comprise an aqueous liquid (e.g., salt solution) used for separating according to specific gravity (according to any of the respective embodiments described herein), as well as aqueous liquid originating in the waste material which is intermixed with the aqueous liquid for separating according to specific gravity, and/or oils originating in the waste material.

Liquids Utilized in Separation Process:

As described herein, the liquid utilized in a separation process according to any of the respective embodiments described herein may be a pure liquid, a solution, or a suspension. In some embodiments of any of the embodiments described herein, the liquid is an aqueous liquid.

As used herein, the phrase "aqueous liquid" refers to a liquid in which at least 50 weight percents of the liquid compound(s) therein (e.g., excluding solid materials suspended and/or dissolved in the liquid) is water. In some embodiments, at least 60 weight percents is water. In some embodiments, at least 70 weight percents is water. In some embodiments, at least 80 weight percents is water. In some embodiments, at least 90 weight percents is water. In some embodiments, at least 95 weight percents is water. In some embodiments, at least 98 weight percents is water. In some embodiments, at least 99 weight percents is water. In some embodiments, the liquid component substantially consists of water.

In some embodiments of any of the embodiments described herein, the liquid is a solution, for example, an aqueous solution. Suitable solutes for a solution (e.g., an aqueous solution) include water-soluble salts, that is, any compound which form ions in water (e.g., sodium chloride, potassium chloride, sodium bromide, potassium bromide, calcium chloride, calcium nitrate, potassium carbonate) and water-soluble carbohydrates (e.g., glucose, sucrose, lactose, fructose).

In some embodiments of any of the embodiments described herein, the solute is a salt, that is, the liquid is an aqueous salt solution (solution of ions). In some embodiments the salt comprises sodium chloride. The sodium chloride may optionally be substantially pure. Alternatively, the sodium chloride is mixed with other salts, for example, as in sea salt.

In some embodiments of any of the embodiments described herein, the liquid comprises sea water (e.g., sea water diluted with fresh water and/or concentrated sea water, that is, sea water from which a portion of the water has been removed). In some embodiments, the liquid consists essentially of sea water.

In some embodiments of any of the embodiments described herein, the liquid is a suspension, for example, an aqueous suspension. Suitable suspended materials for a suspension include water-insoluble salts and/or metallic substances, such as, for example, calcium carbonate, iron powder and ferrosilicon (FeSi). In some embodiments, the suspended material is magnetic, which facilitates removal its removal from separated waste materials (e.g., for reuse).

The specific gravity of a solution or a suspension can be finely controlled in accordance with the separation requirements, by controlling the concentration of the solute or suspended material.

Thus, for example, if a relatively high specific gravity is desired for a fraction of high-density materials, a solution or suspension with a relatively high specific gravity (yet lower than that of the materials to be included in the fraction of high-density materials) is to be used, and therefore, a high concentration of the solute or suspended material is included.

If a relatively low specific gravity (e.g., below that of water) is desired for a fraction of low-density materials (e.g., low-density organic materials), a solution or suspension with a relatively low specific gravity (yet higher than that of the materials to be included in the fraction of low-density materials) is to be used, and therefore, a low concentration (optionally zero) of the solute or suspended material is included.

In some embodiments of any of the embodiments described herein, a specific gravity of a liquid is in a range of from 1.00 to 2.50.

A specific gravity of up to 2.50 may be suitable, for example, for separating all or almost all inorganic materials which may be present in the waste material, for example, by including them in a fraction of high-density materials. Thus, for example, window glass has a specific gravity of approximately 2.58, silica has a specific gravity of approximately 2.65, aluminum has a specific gravity of approximately 2.7, and specific gravities of other minerals and metals are typically even higher. In some of any of the embodiments described herein, the specific gravity of a liquid is at least 2.00, for example, in a range of from 2.00 to 2.50. A specific gravity of at least 2.00 may be suitable, for example, for including all or almost all organic materials, such as plant materials, animal materials, and polymeric materials (e.g., rubber and plastics), in a fraction of low-density materials.

In some embodiments of any of the embodiments described herein, the specific gravity of a liquid is at least 1.50, for example, in a range of from 1.50 to 2.00. A specific gravity of at least 1.50 may be suitable, for including a large majority of organic materials in a fraction of low-density materials. In some embodiments, the specific gravity is at least 1.60. In some embodiments, the specific gravity is at least 1.70. In some embodiments, the specific gravity is at least 1.80. In some embodiments, the specific gravity is at least 1.90.

In some embodiments of any of the embodiments described herein, the specific gravity of a liquid is at least 1.20, for example, in a range of from 1.20 to 1.50. A specific gravity of at least 1.20 may be suitable, for including many or even most organic materials in a fraction of low-density materials, while including some organic materials (e.g., high-density polymeric materials) in a fraction of high-density materials. In some embodiments, the specific gravity of a liquid is at least 1.25. In some embodiments, the specific gravity of a liquid is at least 1.30. In some embodiments, the specific gravity of a liquid is at least 1.35. In some embodiments, the specific gravity of a liquid is at least 1.40. In some embodiments, the specific gravity of a liquid is at least 1.45.

In some embodiments of any of the embodiments described herein, the specific gravity of a liquid is at least 1.01, for example, in a range of from 1.01 to 1.20. A specific gravity in a range of 1.01 to 1.20 may be suitable, for including many or even most animal materials and plant materials (e.g., lignocellulose) in a fraction of low-density materials, while including many synthetic polymers (e.g., high-density polymeric materials), such as thermoset polymers, synthetic polymers having a melting point of at least 250° C. (e.g., polyethylene terephthalate (PET), polytetrafluoroethylene (PTFE)) and polyvinyl chloride (PVC), in a fraction of high-density materials.

Herein, the term "thermoset" refers to a synthetic polymer that has been irreversibly cured by any technique, including curing by heating, by chemical reaction (e.g., as in epoxies) or irradiation. Examples of thermoset polymers include, without limitation, thermoset polyesters (e.g., as used in fiberglass), polyurethanes, vulcanized rubbers, phenol-formaldehydes (e.g., Bakelite® polymer), Duroplast, urea-formaldehydes (e.g., as used in plywood), melamine resins, epoxy resins, polyimides, cyanate esters and polycyanurates.

Without being bound by any particular theory, it is believed that reducing a proportion of thermoset polymers, synthetic polymers having a high melting point (e.g., at least 250° C.) and/or PVC in fraction of low-density materials renders the fraction more amenable to some types of processing (e.g., as described herein). It is further believed that separation according to specific gravity, as described herein, is a particularly convenient method for obtaining a fraction with a reduced proportion of such polymers relative to a waste material from which the fraction is derived.

In some embodiments of any of the embodiments described herein, the specific gravity of the liquid is no more than about 1.25 (e.g., about the specific gravity of a saturated aqueous solution of sea salt). In some embodiments, the specific gravity is no more than 1.20. In some embodiments, the specific gravity is no more than 1.15.

In some embodiments of any of the embodiments described herein, the specific gravity of a liquid is at least 1.05. In some embodiments, the specific gravity is in a range of from 1.05 to 1.25. In some embodiments, the specific gravity is in a range of from 1.05 to 1.20. In some embodiments, the specific gravity is in a range of from 1.05 to 1.15.

In some embodiments of any of the embodiments described herein, the specific gravity of a liquid is at least 1.06. In some embodiments, the specific gravity is in a range of from 1.06 to 1.25. In some embodiments, the specific gravity is in a range of from 1.06 to 1.20. In some embodiments, the specific gravity is in a range of from 1.06 to 1.15.

In some embodiments of any of the embodiments described herein, the specific gravity of a liquid is at least 1.07 (e.g., an aqueous sodium chloride solution at a concentration of about 10 weight percents). In some embodiments, the specific gravity is in a range of from 1.07 to 1.25. In some embodiments, the specific gravity is in a range of from 1.07 to 1.20. In some embodiments, the specific gravity is in a range of from 1.07 to 1.15.

In some embodiments of any of the embodiments described herein, the specific gravity of a liquid is at least 1.08. In some embodiments, the specific gravity is in a range of from 1.08 to 1.25. In some embodiments, the specific gravity is in a range of from 1.08 to 1.20. In some embodiments, the specific gravity is in a range of from 1.08 to 1.15.

In some embodiments of any of the embodiments described herein, the specific gravity of a liquid is at least 1.09. In some embodiments, the specific gravity is in a range of from 1.09 to 1.25. In some embodiments, the specific gravity is in a range of from 1.09 to 1.20. In some embodiments, the specific gravity is in a range of from 1.09 to 1.15.

In some embodiments of any of the embodiments described herein, the specific gravity of a liquid is at least 1.10. In some embodiments, the specific gravity is in a range of from 1.10 to 1.25. In some embodiments, the specific gravity is in a range of from 1.10 to 1.20. In some embodiments, the specific gravity is in a range of from 1.10 to 1.15.

In some embodiments of any of the embodiments described herein, the specific gravity of a liquid is at least 1.11 (e.g., an aqueous sodium chloride solution at a concentration of about 15 weight percents). In some embodiments, the specific gravity is in a range of from 1.11 to 1.25. In some embodiments, the specific gravity is in a range of from 1.11 to 1.20.

In some embodiments of any of the embodiments described herein, the specific gravity of a liquid is at least 1.12. In some embodiments, the specific gravity is in a range of from 1.12 to 1.25. In some embodiments, the specific gravity is in a range of from 1.12 to 1.20.

In some embodiments of any of the embodiments described herein, the specific gravity of a liquid is at least 1.13. In some embodiments, the specific gravity is in a range of from 1.13 to 1.25. In some embodiments, the specific gravity is in a range of from 1.13 to 1.20.

In some embodiments of any of the embodiments described herein, the specific gravity of a liquid is at least 1.14. In some embodiments, the specific gravity is in a range of from 1.14 to 1.25. In some embodiments, the specific gravity is in a range of from 1.14 to 1.20.

In some embodiments of any of the embodiments described herein, the specific gravity of a liquid is at least 1.15 (e.g., an aqueous sodium chloride solution at a concentration of about 20 weight percents). In some embodiments, the specific gravity is in a range of from 1.15 to 1.25. In some embodiments, the specific gravity is in a range of from 1.15 to 1.20.

In some embodiments of any of the embodiments described herein, the specific gravity of a liquid is at least 1.175. In some embodiments, the specific gravity is in a range of from 1.175 to 1.25. In some embodiments, the specific gravity is in a range of from 1.175 to 1.20.

In some embodiments of any of the embodiments described herein, the specific gravity of a liquid is at least 1.20. In some embodiments, the specific gravity is in a range of from 1.20 to 1.25.

In some embodiments of any of the embodiments described herein, the specific gravity of a liquid is approximately 1.03 or less, for example, in a range of from 1.01 to 1.03. A specific gravity in a range may conveniently and inexpensively be obtained, for example, using sea water or diluted sea water, as sea water has a specific gravity in a range of from 1.02 to 1.03, typically approximately 1.025.

In general, liquids with relatively low specific gravities (e.g., up to 1.25, up to 1.20) are relatively convenient to prepare and use, they may readily be obtained from solutions of common and inexpensive materials. For example, specific gravities of aqueous sodium chloride solutions range from 1.00 to about 1.20, depending on concentration. Relatively low specific gravities are particularly suitable for efficiently including inorganic materials in a fraction of high-density materials, including for example, composite materials (e.g., fiberglass and polymers with glass filler) which have a lower specific gravity than pure inorganic materials, as well as high-density polymeric materials such as PVC, PET, PTFE and thermoset polymers (e.g., as described herein).

In some embodiments of any of the embodiments described herein, specific gravities of at least 1.20, optionally at least 1.25, are obtained using high density water-soluble salts such as calcium salts, magnesium salts, transition metal salts, bromide salts and/or using suspensions.

Without being bound by any particular theory, it is believed that contact of waste material with a salt solution inhibits microbial (e.g., bacterial) survival and/or activity in the obtained fractions and/or separated materials (in addition to facilitating the separation process). Such inhibition is comparable to preservation of food in salt water (e.g., pickling). Such inhibition may for example, enhance hygiene and/or reduce malodor of fractions and/or separated materials, thereby and facilitating their handling and/or storage.

In some embodiments of any of the embodiments described herein, a concentration of salt in a solution is selected to be capable of inhibiting microbial (e.g., bacterial) survival and/or activity in waste material contacted with the solution, and/or in fractions, separated material and/or processed material (e.g., as described herein) derived therefrom.

In some embodiments of any of the embodiments described herein, the concentration of salt (e.g., sodium chloride, sea salt) in a salt solution (e.g., aqueous salt solution) is at least 3 weight percents. In some embodiments, the concentration of salt is in a range of from 3 to 35 weight percents. In some embodiments, the concentration of salt is in a range of from 3 to 30 weight percents. In some embodiments, the concentration of salt is in a range of from 3 to 25 weight percents.

In some embodiments of any of the embodiments described herein, the concentration of salt (e.g., sodium chloride, sea salt) in a salt solution (e.g., aqueous salt solution) is at least 5 weight percents. In some embodiments, the concentration of salt is in a range of from 5 to 35 weight percents. In some embodiments, the concentration of salt is in a range of from 5 to 30 weight percents. In some embodiments, the concentration of salt is in a range of from 5 to 25 weight percents.

In some embodiments of any of the embodiments described herein, the concentration of salt (e.g., sodium chloride, sea salt) in a salt solution (e.g., aqueous salt solution) is at least 10 weight percents. In some embodiments, the concentration of salt is in a range of from 10 to 35 weight percents. In some embodiments, the concentration of salt is in a range of from 10 to 30 weight percents. In some embodiments, the concentration of salt is in a range of from 10 to 25 weight percents.

In some embodiments of any of the embodiments described herein, the concentration of salt (e.g., sodium chloride, sea salt) in a salt solution (e.g., aqueous salt solution) is at least 15 weight percents. In some embodiments, the concentration of salt is in a range of from 15 to 35 weight percents. In some embodiments, the concentration of salt is in a range of from 15 to 30 weight percents. In some embodiments, the concentration of salt is in a range of from 15 to 25 weight percents.

In some embodiments of any of the embodiments described herein, the concentration of salt (e.g., sodium chloride, sea salt) in a salt solution (e.g., aqueous salt solution) is at least 20 weight percents. In some embodiments, the concentration of salt is in a range of from 20 to 35 weight percents. In some embodiments, the concentration of salt is in a range of from 20 to 30 weight percents. In some embodiments, the concentration of salt is in a range of from 20 to 25 weight percents.

Without being bound by any particular theory, it is believed that contact of waste material and/or a fraction derived therefrom with a salt solution comprising salt concentrations of at least 10 weight percents, especially at least 15 weight percents, and most especially at least 20 weight percents, is particularly effective at inhibiting microbial (e.g., bacterial) survival and/or activity not only in material contacted with the solution, but also at inhibiting microbial (e.g., bacterial) survival and/or activity in separated material and/or processed material (e.g., as described herein) derived therefrom, that is, residual salt remaining in the separated material and/or processed material (after the material has been removed from the salt solution) can effectively inhibit microbial survival and/or activity long after the separation according to specific gravity has been completed.

It is to be appreciated that cellulose and other compounds from animal material or plant material (e.g., lignin) are characterized by a specific gravity of approximately 1.5, but that animal materials and plant materials typically exhibit considerably lower specific gravities as a result of porosity (for, example, the voids in wood, which reduce the specific gravity of most wood to less than 1) and/or a considerable amount of water therein (which results in a specific gravity close to 1). Thus, a specific gravity of many materials is indicative of its water content and/or porosity.

In some embodiments of any of the embodiments described herein, a fraction of low-density materials (e.g., a third fraction) obtained according to any of the respective embodiments described herein has an (average) specific gravity, for example, less than 1.20, optionally less than 1.15, optionally less than 1.10, optionally less than 1.05, and optionally less than 1.00.

In some embodiments of any of the embodiments described herein, a fraction of low-density materials (e.g., a first fraction) obtained according to any of the respective embodiments described herein contains at least 90 weight percents (dry weight) of an organic material, for example, by selecting a liquid in which inorganic materials sink.

In some embodiments of any of the embodiments described herein, a fraction of low-density materials (e.g., a first fraction) obtained according to any of the respective embodiments described herein contains at least 90 weight percents (dry weight) of an organic material other than thermoset polymers and synthetic polymers having a melting point of at least 250° C. (e.g., PET, PTFE), for example, by selecting a liquid in which such polymers sink.

In some embodiments of any of the embodiments described herein, a fraction of low-density materials (e.g., a first fraction) obtained according to any of the respective embodiments described herein contains at least 90 weight percents (dry weight) of an organic material other than PVC, for example, by selecting a liquid in which PVC sinks.

In some embodiments of any of the embodiments described herein, a fraction of low-density materials (e.g., a first fraction) obtained according to any of the respective embodiments described herein contains at least 90 weight percents (dry weight) of an organic material other than thermoset polymers, synthetic polymers having a melting point of at least 250° C. (e.g., PET, PTFE) and polyvinyl chloride (PVC), for example, by selecting a liquid in which such polymers sink.

In this respect, it is to be appreciated that thermoset polymers, synthetic polymers having a melting point of at least 250° C. (e.g., PET, PTFE) and polyvinyl chloride (PVC) are typically characterized by a relatively high specific gravity.

For example, among synthetic polymers characterized by a melting point of at least 250° C., PET (which is particularly widespread in waste material, e.g., due to its use in food and liquid containers) typically exhibits a specific gravity in a range of from 1.37-1.455 and PTFE typically exhibits a specific gravity in a range of 2.1-2.2.

Similarly, polyvinyl chloride (a widespread polymer) typically exhibits a specific gravity in a range of from 1.35-1.45 in its rigid, relatively pure forms, whereas flexible forms of polyvinyl chloride typically exhibit a lower specific gravity (e.g., in a range of from 1.1-1.3) due to a presence of plasticizers. Thus, a liquid with a specific gravity below 1.1 may be suitable for obtaining substantially all polyvinyl chloride in a fraction of high-density materials (rather than low-density materials), whereas a liquid with a moderately higher specific gravity (e.g., in a range of from 1.1-1.3) may be suitable for obtaining a considerable proportion of polyvinyl chloride in a fraction of high-density materials.

In addition, thermoset polymers typically comprise a considerable amount of heteroatoms (e.g., nitrogen, oxygen, sulfur), for example, in ester groups, urethane groups, and sulfur cross-links of vulcanized rubber, which increase the specific gravity of the polymer.

It is to be appreciated that contacting waste material with a liquid (according to any of the respective embodiments described herein) may effect partial removal of liquids which originate in the waste material and are miscible with the liquid for separating according to specific gravity, as the liquids remain intermixed when a separated material is removed from the liquids. For example, aqueous liquids in a source waste material may optionally be at least partially removed upon contact with an aqueous liquid (e.g., salt solution) according to any of the respective embodiments described herein.

Low-density Polymeric Material:

In some embodiments of any of the embodiments described herein, one of the plurality of separated materials obtained is a low-density polymeric material. In some such embodiments, at least one other separated material is a high-density polymeric material, a metal, a glass, an oil, and lignocellulose.

In some of any of the embodiments described herein, a fraction of low-density materials (according to any of the respective embodiments described herein) is the separated low-density polymeric material (the fraction being a polymeric material as defined herein).

In some of any of the embodiments described herein, a third fraction of low-density materials (according to any of the respective embodiments described herein) is the separated low-density polymeric material (the third fraction being a polymeric material as defined herein).

In some of any of the embodiments described herein, a fraction of low-density materials which is the separated low-density polymeric material is obtained by separating material (waste material or a fraction thereof) in a liquid having a specific gravity of no more than 1.03 (according to any of the embodiments herein pertaining to such a liquid). In some such embodiments, the specific gravity of the liquid is no more than 1.02 (according to any of the embodiments herein pertaining to such a liquid). In some such embodiments, the specific gravity of the liquid is no more than 1.01 (according to any of the embodiments herein pertaining to such a liquid). In some such embodiments, the specific gravity of the liquid is no more than 1.00 (according to any of the embodiments herein pertaining to such a liquid). In some such embodiments, the liquid is water.

Typically, the low-density polymeric material comprises, in significant proportions, at least a portion of the synthetic polymers in the waste material.

Without being bound by any particular theory, it is believed that synthetic polymers comprise a substantial portion of the polymers in low-density polymeric material, due to the relatively low specific gravity of many synthetic polymers.

Herein throughout, the phrase "synthetic polymers" refers to polymers other than those found in plant or animal material (e.g., lignin, carbohydrates, polypeptides) or polymers formed from processing of plant or animal material in a manner which alters a chemical composition of the polymer. Examples of synthetic polymers include, without limitation, polyolefins, polystyrene, polyvinylchloride, polyethylene terephthalate, polyacrylonitrile, polybutadiene, polystyrene, polycarbonate, polyesters (e.g., rayon), and nylon. Polymers formed by chemical reactions of a natural polymer, for example, cellulose which has been chemically treated (e.g., by carbon disulfide) and regenerated to form rayon, are considered herein to be synthetic polymers, as are products of hydrolysis, caramelization and/or pyrolysis of carbohydrates, polypeptides, etc. The skilled person will be aware of additional synthetic polymers which may be found in waste material, and which consequently may be included in a low-density polymeric material and/or high-density polymeric material described herein.

In some of any of the embodiments described herein, at least 50 weight percents of the low-density polymeric material is synthetic polymers (by dry weight). In some embodiments, at least 60 weight percents of the low-density polymeric material is synthetic polymers (by dry weight). In some embodiments, at least 70 weight percents of the low-density polymeric material is synthetic polymers (by dry weight). In some embodiments, at least 80 weight percents of the low-density polymeric material is synthetic polymers (by dry weight). In some embodiments, at least 90 weight percents of the low-density polymeric material is synthetic polymers (by dry weight). In some embodiments, at least 95 weight percents of the low-density polymeric material is synthetic polymers (by dry weight).

Without being bound by any particular theory, it is believed that polyolefins will comprise a substantial portion of the low-density polymeric material, due to the relatively low specific gravity of polyolefins.

Herein, the term "polyolefin" refers to a polymer prepared from an olefin monomer. Examples of polyolefins include, without limitation, polyethylene, polypropylene, polymethylpentene, polybutene-1, polyisobutylene, ethylene propylene rubber, ethylene propylene diene monomer rubber, and copolymers thereof. Polyethylene and polypropylene are particularly common in waste material, and therefore likely to be present in substantial amounts in separated material such as low-density polymeric material.

In some of any of the embodiments described herein, at least 50 weight percents of the low-density polymeric material is polyolefins (by dry weight). In some embodiments, at least 60 weight percents of the low-density polymeric material is polyolefins (by dry weight). In some embodiments, at least 70 weight percents of the low-density polymeric material is polyolefins (by dry weight). In some embodiments, at least 80 weight percents of the low-density polymeric material is polyolefins (by dry weight). In some embodiments, at least 90 weight percents of the low-density polymeric material is polyolefins (by dry weight).

In some of any of the embodiments described herein, at least 50 weight percents of the low-density polymeric material is synthetic polymers, and at least 50 weight percents of the synthetic polymers in the low-density polymeric material is polyolefins (by dry weight). In some such embodiments, at least 60 weight percents of the synthetic polymers in the low-density polymeric material is polyolefins (by dry weight). In some such embodiments, at least 70 weight percents of the synthetic polymers in the low-density polymeric material is polyolefins (by dry weight). In some such embodiments, at least 80 weight percents of the synthetic polymers in the low-density polymeric material is polyolefins (by dry weight). In some such embodiments, at least 90 weight percents of the synthetic polymers in the low-density polymeric material is polyolefins (by dry weight). In some such embodiments, at least 95 weight percents of the synthetic polymers in the low-density polymeric material is polyolefins (by dry weight).

In some of any of the embodiments described herein, at least 60 weight percents of the low-density polymeric material is synthetic polymers, and at least 50 weight percents of the synthetic polymers in the low-density polymeric material is polyolefins (by dry weight). In some such embodiments, at least 60 weight percents of the synthetic polymers in the low-density polymeric material is polyolefins (by dry weight). In some such embodiments, at least 70 weight percents of the synthetic polymers in the low-density polymeric material is polyolefins (by dry weight). In some such embodiments, at least 80 weight percents of the synthetic polymers in the low-density polymeric material is polyolefins (by dry weight). In some such embodiments, at least 90 weight percents of the synthetic polymers in the low-density polymeric material is polyolefins (by dry weight). In some such embodiments, at least 95 weight percents of the synthetic polymers in the low-density polymeric material is polyolefins (by dry weight).

In some of any of the embodiments described herein, at least 70 weight percents of the low-density polymeric material is synthetic polymers, and at least 50 weight percents of the synthetic polymers in the low-density polymeric material is polyolefins (by dry weight). In some such embodiments, at least 60 weight percents of the synthetic polymers in the low-density polymeric material is polyolefins (by dry weight). In some such embodiments, at least 70 weight percents of the synthetic polymers in the low-density polymeric material is polyolefins (by dry weight). In some such embodiments, at least 80 weight percents of the synthetic polymers in the low-density polymeric material is polyolefins (by dry weight). In some such embodiments, at least 90 weight percents of the synthetic polymers in the low-density polymeric material is polyolefins (by dry weight). In some such embodiments, at least 95 weight percents of the synthetic polymers in the low-density polymeric material is polyolefins (by dry weight).

In some of any of the embodiments described herein, at least 80 weight percents of the low-density polymeric material is synthetic polymers, and at least 50 weight percents of the synthetic polymers in the low-density polymeric material is polyolefins (by dry weight). In some such embodiments, at least 60 weight percents of the synthetic polymers in the low-density polymeric material is polyolefins (by dry weight). In some such embodiments, at least 70 weight percents of the synthetic polymers in the low-density polymeric material is polyolefins (by dry weight). In some such embodiments, at least 80 weight percents of the synthetic polymers in the low-density polymeric material is polyolefins (by dry weight). In some such embodiments, at least 90 weight percents of the synthetic polymers in the low-density polymeric material is polyolefins (by dry weight). In some such embodiments, at least 95 weight percents of the synthetic polymers in the low-density polymeric material is polyolefins (by dry weight).

In some of any of the embodiments described herein, at least 90 weight percents of the low-density polymeric material is synthetic polymers, and at least 50 weight percents of the synthetic polymers in the low-density polymeric material is polyolefins (by dry weight). In some such embodiments, at least 60 weight percents of the synthetic polymers in the low-density polymeric material is polyolefins (by dry weight). In some such embodiments, at least 70 weight percents of the synthetic polymers in the low-density polymeric material is polyolefins (by dry weight). In some such embodiments, at least 80 weight percents of the synthetic polymers in the low-density polymeric material is polyolefins (by dry weight). In some such embodiments, at least 90 weight percents of the synthetic polymers in the low-density polymeric material is polyolefins (by dry weight). In some such embodiments, at least 95 weight percents of the synthetic polymers in the low-density polymeric material is polyolefins (by dry weight).

In some of any of the embodiments described herein, at least 95 weight percents of the low-density polymeric material is synthetic polymers, and at least 50 weight percents of the synthetic polymers in the low-density polymeric material is polyolefins (by dry weight). In some such embodiments, at least 60 weight percents of the synthetic polymers in the low-density polymeric material is polyolefins (by dry weight). In some such embodiments, at least 70 weight percents of the synthetic polymers in the low-density polymeric material is polyolefins (by dry weight). In some such embodiments, at least 80 weight percents of the synthetic polymers in the low-density polymeric material is polyolefins (by dry weight). In some such embodiments, at least 90 weight percents of the synthetic polymers in the low-density polymeric material is polyolefins (by dry weight). In some such embodiments, at least 95 weight percents of the synthetic polymers in the low-density polymeric material is polyolefins (by dry weight).

Without being bound by any particular theory, it is believed that thermoplastic polymers comprise a substantial portion of the separated low-density polymeric material, due to the relatively low specific gravity of many thermoplastic polymers, including, but not limited to thermoplastic polyolefins (e.g., polyethylene, polypropylene, polymethylpentene, polybutene-1). It is further believed that thermoplastic polymers, particularly thermoplastic synthetic polymers, facilitate processing (e.g., recycling) of the low-density polymeric material (e.g., wherein processing includes heating), rendering it a particularly useful separated material.

Furthermore, the presence of one or more thermoplastic polymers may optionally enhance the thermoplasticity of a processed material formed by processing the low-density polymeric material (e.g., a processed polymeric material described herein).

Herein throughout, "thermoplastic" refers to an ability to undergo a reversible transition to a deformable state when heated. The deformable state may be, for example, a liquid which results from melting upon heating, or a softened solid or semi-solid, which may be readily deformed (as plastic deformation) by application of pressure.

In some of any of the embodiments pertaining to a method of processing waste material as described herein, at least 50 weight percents of the low-density polymeric material is thermoplastic polymers (by dry weight). In some embodiments, at least 60 weight percents of the low-density polymeric material is thermoplastic polymers (by dry weight). In some embodiments, at least 70 weight percents of the low-density polymeric material is thermoplastic polymers (by dry weight). In some embodiments, at least 80 weight percents of the low-density polymeric material is thermoplastic polymers (by dry weight). In some embodiments, at least 90 weight percents of the low-density polymeric material is thermoplastic polymers (by dry weight). In some embodiments, at least 95 weight percents of the low-density polymeric material is thermoplastic polymers (by dry weight).

Lignocellulose:

In some embodiments of any of the embodiments described herein, one of the plurality of separated materials obtained is lignocellulose, also referred to herein interchangeably as "separated lignocellulose". In some such embodiments, at least one other separated material is a high-density polymeric material, a metal, a glass, an oil, and a low-density polymeric material.

In some of any of the embodiments described herein, a fourth fraction of intermediate-density materials (according to any of the respective embodiments described herein) is the separated lignocellulose.

Herein throughout, in the context of describing a separated material which is lignocellulose (e.g., as described by the term "separated lignocellulose"), the separated material may comprise impurities (material other than lignocellulose), provided that at least 50 weight percents (by dry weight) of the separated material is lignocellulose (as defined herein) per se.

As used herein, the term "lignocellulose" (per se, rather than in a context of a separated lignocellulose, as defined herein) refers to dry matter derived from plants, which is composed primarily of carbohydrates (primarily cellulose and hemicelluloses) and lignin. Thus, an amount of lignocellulose described herein may be considered a total amount of dry matter derived from plants, regardless of the proportions of, e.g., carbohydrates and lignin. Lignocellulose is also referred to in the art as "ligneous cellulose".

Without being bound by any particular theory, it is believed that the carbohydrates in lignocelluloses (e.g., cellulose and/or hemicelluloses) are particularly amenable to processing as described herein (e.g., as compared to lignin), including, without limitation, fermentation and/or microbial digestion processes (e.g., as described herein). The proportion of carbohydrates in the lignocellulose may optionally be enhanced by limiting an amount of lignin-rich material in the waste material being processed, for example, by using waste material with no more than a limited amount of wood (e.g., tree trimmings, lumberyard waste).

In some of any of the embodiments described herein, from 50 to 95 weight percents of the dry weight of a separated lignocellulose (as defined herein) is lignocellulose. In some embodiments, from 50 to 90 weight percents of the dry weight is lignocellulose. In some embodiments, from 50 to 85 weight percents of the dry weight is lignocellulose. In some embodiments, from 50 to 80 weight percents of the dry weight is lignocellulose. In some embodiments, from 50 to 75 weight percents of the dry weight is lignocellulose. In some embodiments, from 50 to 70 weight percents of the dry weight is lignocellulose. In some such embodiments, at least 40 weight percents of the lignocellulose per se is carbohydrates. In some embodiments, at least 60 weight percents of the lignocellulose per se is carbohydrates. In some embodiments, at least 80 weight percents of the lignocellulose per se is carbohydrates. In some embodiments, at least 90 weight percents of the lignocellulose per se is carbohydrates.

In some of any of the embodiments described herein, at least 60 weight percents of the dry weight of a separated lignocellulose (as defined herein) is lignocellulose. In some embodiments, from 60 to 95 weight percents of the dry weight is lignocellulose. In some embodiments, from 60 to 90 weight percents of the dry weight is lignocellulose. In some embodiments, from 60 to 85 weight percents of the dry weight is lignocellulose. In some embodiments, from 60 to 80 weight percents of the dry weight is lignocellulose. In some embodiments, at least 40 weight percents of the lignocellulose per se is carbohydrates. In some embodiments, at least 60 weight percents of the lignocellulose per se is carbohydrates. In some embodiments, at least 80 weight percents of the lignocellulose per se is carbohydrates. In some embodiments, at least 90 weight percents of the lignocellulose per se is carbohydrates.

In some of any of the embodiments described herein, at least 70 weight percents of the dry weight of a separated lignocellulose (as defined herein) is lignocellulose. In some embodiments, from 70 to 95 weight percents of the dry weight is lignocellulose. In some embodiments, from 70 to 90 weight percents of the dry weight is lignocellulose. In some embodiments, from 70 to 85 weight percents of the dry weight is lignocellulose. In some embodiments, from 75 to 85 weight percents of the dry weight is lignocellulose. In some such embodiments, at least 40 weight percents of the lignocellulose per se is carbohydrates. In some embodiments, at least 60 weight percents of the lignocellulose per se is carbohydrates. In some embodiments, at least 80 weight percents of the lignocellulose per se is carbohydrates. In some embodiments, at least 90 weight percents of the lignocellulose per se is carbohydrates.

In some of any of the embodiments described herein, at least 80 weight percents of the dry weight of a separated lignocellulose (as defined herein) is lignocellulose. In some embodiments, from 80 to 95 weight percents of the dry weight is lignocellulose. In some embodiments, from 80 to 90 weight percents of the dry weight is lignocellulose. In some embodiments, from 80 to 85 weight percents of the dry weight is lignocellulose. In some such embodiments, at least 40 weight percents of the lignocellulose per se is carbohydrates. In some embodiments, at least 60 weight percents of the lignocellulose per se is carbohydrates. In some embodiments, at least 80 weight percents of the lignocellulose per se is carbohydrates. In some embodiments, at least 90 weight percents of the lignocellulose per se is carbohydrates.

In some of any of the embodiments described herein, at least 90 weight percents of the dry weight of a separated lignocellulose (as defined herein) is lignocellulose. In some embodiments, from 90 to 95 weight percents of the dry weight is lignocellulose. In some such embodiments, at least 40 weight percents of the lignocellulose per se is carbohydrates. In some embodiments, at least 60 weight percents of the lignocellulose per se is carbohydrates. In some embodiments, at least 80 weight percents of the lignocellulose per se is carbohydrates. In some embodiments, at least 90 weight percents of the lignocellulose per se is carbohydrates.

In some of any of the embodiments described herein, at least 95 weight percents of the dry weight of a separated lignocellulose (as defined herein) is lignocellulose. In some such embodiments, at least 40 weight percents of the lignocellulose per se is carbohydrates. In some embodiments, at least 60 weight percents of the lignocellulose per se is carbohydrates. In some embodiments, at least 80 weight percents of the lignocellulose per se is carbohydrates. In some embodiments, at least 90 weight percents of the lignocellulose per se is carbohydrates.

In some of any of the embodiments described herein, a fourth fraction of intermediate-density materials which is the separated lignocellulose is obtained by separating material (waste material or a fraction thereof) in a liquid having a specific gravity of no more than 1.03 (in which the intermediate-density materials sink) and in a liquid having a specific gravity of at least 1.05 (in which the intermediate-density materials do not sink), as described in any of the embodiments herein pertaining to such liquids. In some such embodiments, the specific gravity of the liquid in which the intermediate-density materials sink is no more than 1.02

(according to any of the embodiments herein pertaining to such a liquid). In some such embodiments, the specific gravity of the liquid in which the intermediate-density materials sink is no more than 1.01 (according to any of the embodiments herein pertaining to such a liquid). In some such embodiments, the specific gravity of the liquid in which the intermediate-density materials sink is no more than 1.00 (according to any of the embodiments herein pertaining to such a liquid). In some such embodiments, the liquid in which the intermediate-density materials sink is water.

In some of any of the embodiments described herein, a fourth fraction of intermediate-density materials which is the separated lignocellulose is obtained by separating material (waste material or a fraction thereof) in a liquid having a specific gravity of no more than 1.03 (in which the intermediate-density materials sink) and in a liquid having a specific gravity of at least 1.06 (in which the intermediate-density materials do not sink), as described in any of the embodiments herein pertaining to such liquids. In some such embodiments, the specific gravity of the liquid in which the intermediate-density materials sink is no more than 1.02 (according to any of the embodiments herein pertaining to such a liquid). In some such embodiments, the specific gravity of the liquid in which the intermediate-density materials sink is no more than 1.01 (according to any of the embodiments herein pertaining to such a liquid). In some such embodiments, the specific gravity of the liquid in which the intermediate-density materials sink is no more than 1.00 (according to any of the embodiments herein pertaining to such a liquid). In some such embodiments, the liquid in which the intermediate-density materials sink is water.

In some of any of the embodiments described herein, a fourth fraction of intermediate-density materials which is the separated lignocellulose is obtained by separating material (waste material or a fraction thereof) in a liquid having a specific gravity of no more than 1.03 (in which the intermediate-density materials sink) and in a liquid having a specific gravity of at least 1.07 (in which the intermediate-density materials do not sink), as described in any of the embodiments herein pertaining to such liquids. In some such embodiments, the specific gravity of the liquid in which the intermediate-density materials sink is no more than 1.02 (according to any of the embodiments herein pertaining to such a liquid). In some such embodiments, the specific gravity of the liquid in which the intermediate-density materials sink is no more than 1.01 (according to any of the embodiments herein pertaining to such a liquid). In some such embodiments, the specific gravity of the liquid in which the intermediate-density materials sink is no more than 1.00 (according to any of the embodiments herein pertaining to such a liquid). In some such embodiments, the liquid in which the intermediate-density materials sink is water.

In some of any of the embodiments described herein, a fourth fraction of intermediate-density materials which is the separated lignocellulose is obtained by separating material (waste material or a fraction thereof) in a liquid having a specific gravity of no more than 1.03 (in which the intermediate-density materials sink) and in a liquid having a specific gravity of at least 1.08 (in which the intermediate-density materials do not sink), as described in any of the embodiments herein pertaining to such liquids. In some such embodiments, the specific gravity of the liquid in which the intermediate-density materials sink is no more than 1.02 (according to any of the embodiments herein pertaining to such a liquid). In some such embodiments, the specific gravity of the liquid in which the intermediate-density materials sink is no more than 1.01 (according to any of the embodiments herein pertaining to such a liquid). In some such embodiments, the specific gravity of the liquid in which the intermediate-density materials sink is no more than 1.00 (according to any of the embodiments herein pertaining to such a liquid). In some such embodiments, the liquid in which the intermediate-density materials sink is water.

In some of any of the embodiments described herein, a fourth fraction of intermediate-density materials which is the separated lignocellulose is obtained by separating material (waste material or a fraction thereof) in a liquid having a specific gravity of no more than 1.03 (in which the intermediate-density materials sink) and in a liquid having a specific gravity of at least 1.09 (in which the intermediate-density materials do not sink), as described in any of the embodiments herein pertaining to such liquids. In some such embodiments, the specific gravity of the liquid in which the intermediate-density materials sink is no more than 1.02 (according to any of the embodiments herein pertaining to such a liquid). In some such embodiments, the specific gravity of the liquid in which the intermediate-density materials sink is no more than 1.01 (according to any of the embodiments herein pertaining to such a liquid). In some such embodiments, the specific gravity of the liquid in which the intermediate-density materials sink is no more than 1.00 (according to any of the embodiments herein pertaining to such a liquid). In some such embodiments, the liquid in which the intermediate-density materials sink is water.

In some of any of the embodiments described herein, a fourth fraction of intermediate-density materials which is the separated lignocellulose is obtained by separating material (waste material or a fraction thereof) in a liquid having a specific gravity of no more than 1.03 (in which the intermediate-density materials sink) and in a liquid having a specific gravity of at least 1.10 (in which the intermediate-density materials do not sink), as described in any of the embodiments herein pertaining to such liquids. In some such embodiments, the specific gravity of the liquid in which the intermediate-density materials sink is no more than 1.02 (according to any of the embodiments herein pertaining to such a liquid). In some such embodiments, the specific gravity of the liquid in which the intermediate-density materials sink is no more than 1.01 (according to any of the embodiments herein pertaining to such a liquid). In some such embodiments, the specific gravity of the liquid in which the intermediate-density materials sink is no more than 1.00 (according to any of the embodiments herein pertaining to such a liquid). In some such embodiments, the liquid in which the intermediate-density materials sink is water.

In some of any of the embodiments described herein, a fourth fraction of intermediate-density materials which is the separated lignocellulose is obtained by separating material (waste material or a fraction thereof) in a liquid having a specific gravity of no more than 1.03 (in which the intermediate-density materials sink) and in a liquid having a specific gravity of at least 1.11 (in which the intermediate-density materials do not sink), as described in any of the embodiments herein pertaining to such liquids. In some such embodiments, the specific gravity of the liquid in which the intermediate-density materials sink is no more than 1.02 (according to any of the embodiments herein pertaining to such a liquid). In some such embodiments, the specific gravity of the liquid in which the intermediate-density materials sink is no more than 1.01 (according to any of the embodiments herein pertaining to such a liquid). In some such embodiments, the specific gravity of the liquid in which the intermediate-density materials sink is no more than 1.00 (according to any of the embodiments herein pertaining to such a liquid). In some such embodiments, the liquid in which the intermediate-density materials sink is water.

In some of any of the embodiments described herein, a fourth fraction of intermediate-density materials which is the separated lignocellulose is obtained by separating material (waste material or a fraction thereof) in a liquid having a specific gravity of no more than 1.03 (in which the intermediate-density materials sink) and in a liquid having a specific gravity of at least 1.12 (in which the intermediate-density materials do not sink), as described in any of the embodiments herein pertaining to such liquids. In some such embodiments, the specific gravity of the liquid in which the intermediate-density materials sink is no more than 1.02 (according to any of the embodiments herein pertaining to such a liquid). In some such embodiments, the specific gravity of the liquid in which the intermediate-density materials sink is no more than 1.01 (according to any of the embodiments herein pertaining to such a liquid). In some such embodiments, the specific gravity of the liquid in which the intermediate-density materials sink is no more than 1.00 (according to any of the embodiments herein pertaining to such a liquid). In some such embodiments, the liquid in which the intermediate-density materials sink is water.

In some of any of the embodiments described herein, a fourth fraction of intermediate-density materials which is the separated lignocellulose is obtained by separating material (waste material or a fraction thereof) in a liquid having a specific gravity of no more than 1.03 (in which the intermediate-density materials sink) and in a liquid having a specific gravity of at least 1.13 (in which the intermediate-density materials do not sink), as described in any of the embodiments herein pertaining to such liquids. In some such embodiments, the specific gravity of the liquid in which the intermediate-density materials sink is no more than 1.02 (according to any of the embodiments herein pertaining to such a liquid). In some such embodiments, the specific gravity of the liquid in which the intermediate-density materials sink is no more than 1.01 (according to any of the embodiments herein pertaining to such a liquid). In some such embodiments, the specific gravity of the liquid in which the intermediate-density materials sink is no more than 1.00 (according to any of the embodiments herein pertaining to such a liquid). In some such embodiments, the liquid in which the intermediate-density materials sink is water.

In some of any of the embodiments described herein, a fourth fraction of intermediate-density materials which is the separated lignocellulose is obtained by separating material (waste material or a fraction thereof) in a liquid having a specific gravity of no more than 1.03 (in which the intermediate-density materials sink) and in a liquid having a specific gravity of at least 1.14 (in which the intermediate-density materials do not sink), as described in any of the embodiments herein pertaining to such liquids. In some such embodiments, the specific gravity of the liquid in which the intermediate-density materials sink is no more than 1.02 (according to any of the embodiments herein pertaining to such a liquid). In some such embodiments, the specific gravity of the liquid in which the intermediate-density materials sink is no more than 1.01 (according to any of the embodiments herein pertaining to such a liquid). In some such embodiments, the specific gravity of the liquid in which the intermediate-density materials sink is no more than 1.00 (according to any of the embodiments herein pertaining to such a liquid). In some such embodiments, the liquid in which the intermediate-density materials sink is water.

In some of any of the embodiments described herein, a fourth fraction of intermediate-density materials which is the separated lignocellulose is obtained by separating material (waste material or a fraction thereof) in a liquid having a specific gravity of no more than 1.03 (in which the intermediate-density materials sink) and in a liquid having a specific gravity of at least 1.15 (in which the intermediate-density materials do not sink), as described in any of the embodiments herein pertaining to such liquids. In some such embodiments, the specific gravity of the liquid in which the intermediate-density materials sink is no more than 1.02 (according to any of the embodiments herein pertaining to such a liquid). In some such embodiments, the specific gravity of the liquid in which the intermediate-density materials sink is no more than 1.01 (according to any of the embodiments herein pertaining to such a liquid). In some such embodiments, the specific gravity of the liquid in which the intermediate-density materials sink is no more than 1.00 (according to any of the embodiments herein pertaining to such a liquid). In some such embodiments, the liquid in which the intermediate-density materials sink is water.

In some of any of the embodiments described herein, a fourth fraction of intermediate-density materials which is the separated lignocellulose is obtained by separating material (waste material or a fraction thereof) in a liquid having a specific gravity of no more than 1.03 (in which the intermediate-density materials sink) and in a liquid having a specific gravity of at least 1.175 (in which the intermediate-density materials do not sink), as described in any of the embodiments herein pertaining to such liquids. In some such embodiments, the specific gravity of the liquid in which the intermediate-density materials sink is no more than 1.02 (according to any of the embodiments herein pertaining to such a liquid). In some such embodiments, the specific gravity of the liquid in which the intermediate-density materials sink is no more than 1.01 (according to any of the embodiments herein pertaining to such a liquid). In some such embodiments, the specific gravity of the liquid in which the intermediate-density materials sink is no more than 1.00 (according to any of the embodiments herein pertaining to such a liquid). In some such embodiments, the liquid in which the intermediate-density materials sink is water.

In some of any of the embodiments described herein, a fourth fraction of intermediate-density materials which is the separated lignocellulose is obtained by separating material (waste material or a fraction thereof) in a liquid having a specific gravity of no more than 1.03 (in which the intermediate-density materials sink) and in a liquid having a specific gravity of at least 1.20 (in which the intermediate-density materials do not sink), as described in any of the embodiments herein pertaining to such liquids. In some such embodiments, the specific gravity of the liquid in which the intermediate-density materials sink is no more than 1.02 (according to any of the embodiments herein pertaining to such a liquid). In some such embodiments, the specific gravity of the liquid in which the intermediate-density materials sink is no more than 1.01 (according to any of the embodiments herein pertaining to such a liquid). In some such embodiments, the specific gravity of the liquid in which the intermediate-density materials sink is no more than 1.00 (according to any of the embodiments herein pertaining to such a liquid). In some such embodiments, the liquid in which the intermediate-density materials sink is water.

In some of any of the embodiments described herein, a fourth fraction of intermediate-density materials which is the separated lignocellulose is obtained by separating material (waste material or a fraction thereof) in a liquid having a specific gravity of no more than 1.01 (in which the intermediate-density materials sink) and in a liquid having a specific gravity of at least 1.03 (in which the intermediate-density materials do not sink), as described in any of the embodiments herein pertaining to such liquids. In some such embodiments, the specific gravity of the liquid in which the intermediate-density materials sink is no more than 1.00 (according to any of the embodiments herein pertaining to such a liquid). In some such embodiments, the liquid in which the intermediate-density materials sink is water.

In some of any of the embodiments described herein, a fourth fraction of intermediate-density materials which is the separated lignocellulose is obtained by separating material (waste material or a fraction thereof) in a liquid having a specific gravity of no more than 1.03 (in which the intermediate-density materials sink) and in a liquid having a specific gravity of no more than 1.30 (in which the intermediate-density materials do not sink), for example, in a range of from 1.03 to 1.30, as described in any of the embodiments herein pertaining to such liquids. In some such embodiments, the specific gravity of the liquid in which the intermediate-density materials sink is no more than 1.02 (according to any of the embodiments herein pertaining to such a liquid). In some such embodiments, the specific gravity of the liquid in which the intermediate-density materials sink is no more than 1.01 (according to any of the embodiments herein pertaining to such a liquid). In some such embodiments, the specific gravity of the liquid in which the intermediate-density materials sink is no more than 1.00 (according to any of the embodiments herein pertaining to such a liquid). In some such embodiments, the liquid in which the intermediate-density materials sink is water.

Microbial Digestion/Fermentation:

In some embodiments of any of the embodiments described herein, the method further comprises subjecting at least a portion of a fraction of material derived from waste material to a microbial digestion/fermentation process. Preferably, the material subjected to a microbial digestion/fermentation process is rich in lignocellulose.

Thus, a microbial digestion/fermentation process as described herein may be regarded as a form of processing, as defined herein, and a desired product of a microbial digestion/fermentation process as described herein may be regarded as a processed material.

In some embodiments of any of the embodiments described herein, at least a portion of a first fraction of low-density materials (according to any of the respective embodiments described herein) is subjected to a microbial digestion/fermentation process, for example, wherein a first fraction of low-density materials is richer in lignocellulose than a second fraction of high-density materials.

In some embodiments of any of the embodiments described herein, at least a portion of a fourth fraction of intermediate-density materials (according to any of the respective embodiments described herein), optionally substantially all of the fourth fraction, is subjected to a microbial digestion/fermentation process, for example, wherein a fourth fraction of low-density materials is richer in lignocellulose than a third fraction of low-density materials and/or a fifth fraction of high-density materials.

In some embodiments of any of the embodiments described herein, at least a portion of a separated lignocellulose (according to any of the respective embodiments described herein), optionally substantially all of the separated lignocellulose, is subjected to a microbial digestion/fermentation process.

The microbial digestion/fermentation process is optionally selected to produce any commercial product obtainable by a fermentation process, including, without limitation, a biogas and/or ethanol.

A skilled person will be capable of selecting a microbial digestion/fermentation process according to a desired product, for example, by selecting one or more appropriate organisms, by controlling conditions under which the fermentation proceeds, and/or by selecting a suitable technique for extracting a desired fermentation product, utilizing techniques known in the art.

In some embodiments of any of the embodiments described herein, processing a separated lignocellulose to produce biogas or ethanol is effected by subjecting at least one fraction which comprises a separated lignocellulose, as described herein, to digestion by organisms and/or by enzymes related thereto, collectively referred to herein as "microbial digestion".

Herein, the term "microbial digestion" refers to use of organisms, preferably microorganisms, to metabolize at least a portion of a material subjected to digestion into different material(s), for example, compounds not present in the original material in an isolated form. A microbial digestion can involve processes performed by the organism as a whole or by enzymes related to the organism, which can be either isolated from the microorganism or not.

In some of any of the embodiments described herein, the microbial digestion is an anaerobic microbial digestion, also referred to herein as "anaerobic digestion", which is performed under conditions in which oxygen is absent.

The term "microorganisms" as used herein includes bacteria, archaea, fungi, protozoa, and other microorganisms known to one of skill in the art to digest lignocellulosic biomass to produce biogas.

Herein, "fermentation" is used describe an anaerobic digestion which is effected by yeast and/or related enzymes, so as to produce ethanol from soluble carbohydrates (sugars).

Microbial digestion of lignocellulosic biomass is beneficially performed for producing a biogas and/or ethanol (e.g., bioethanol), depending on the organism used for effecting the digestion and further on the composition of the biomass and process conditions.

A skilled person will be capable of selecting a microbial digestion process according to a desired product, for example, by selecting one or more appropriate organisms, by controlling conditions under which the microbial digestion proceeds, and/or by selecting a suitable technique for extracting a desired product, utilizing techniques known in the art.

In some of any of the embodiments described herein, a method as described herein is used for producing biogas such as carbon dioxide and/or methanol, and is effected by anaerobic microbial digestion using any of the microorganisms known in the art to effect biogas production from biomass. Typically, biogas production by microbial digestion is effected by a combination of microorganisms, which can be introduced into a single bioreactor, or by means of a plurality of reactors, each comprising different one or more of the microorganisms participating in the production of biogas.

Typically, an anaerobic digestion process generally begins with bacterial hydrolysis of the lignocellulose. Insoluble carbohydrates such as cellulose and hemicellulose are broken down to soluble derivatives that become available for other bacteria. During the hydrolysis stage, simple sugars, amino acids, and fatty acids are produced.

Acidogenic bacteria then convert the sugars and amino acids into carbon dioxide, hydrogen sulfide, ammonia, and organic acids, typically volatile fatty acids.

The third stage of anaerobic digestion is acetogenesis, in which the molecules produced through the acidogenesis phase are further digested by acetogens to produce mainly acetic acid, as well as carbon dioxide and hydrogen.

Finally, methanogens convert the intermediate products of any of the preceding stages into methane, carbon dioxide, and water.

In some of any of the embodiments described herein, a method as described herein is used for producing ethanol (also referred to as bioethanol), and is effected by fermentation using any of the enzymes and/or yeasts known in the art to effect ethanol production from soluble carbohydrates (e.g., soluble sugars such as glucose or xylose).

A fermentation process typically starts by breaking down the lignocellulose into complex sugars, typically by means of acidic solution or by microbial enzymes. A glucoamylase is then added to break the complex sugars down into simple sugars. Thereafter, yeasts are typically added to convert the simple sugars to ethanol, which is can then be separated by distillation. Typically, the yeast species *Saccharomyces cerevisiae*, and optionally genetically engineered mutants thereof, is used to convert carbohydrates to carbon dioxide and ethanol. Other microorganisms which are usable in fermentation to produce ethanol include, but are not limited to, *Zymomonas mobilis*, and *Schizosaccharomyces*.

Microbial digestion/fermentation will typically yield an organic residue in addition to a product described herein, the organic residue remaining after the product obtained by the fermentation process has been collected.

In some embodiments of any of the embodiments described herein, the method further comprises preparing a compost from an organic residue remaining after a microbial digestion/fermentation process according to any of the respective embodiments described herein.

Herein, the phrase "preparing a compost" refers to at least collecting ingredients of the compost, the compost optionally consisting essentially of an organic residue described herein, or alternatively, the compost comprises one or more additional materials suitable for use in a compost, mixed with the organic residue.

Without being bound by any particular theory, it is believed that the organic residue described herein has a greater ratio of lignin to carbohydrates than does the material subjected to a microbial digestion/fermentation process, as metabolism of carbohydrates in lignocellulose occurs more readily than metabolism of lignin.

It is further believed that the organic residue comprises a considerable proportion of substances which are slowly metabolized by microorganisms, wherein the slow metabolism is too slow to be suitable for being utilized in an industrial microbial digestion/fermentation process (e.g., as described herein), yet is highly suitable for applications in which slow metabolism is suitable, for such as use in a compost.

According to another aspect of embodiments of the invention, there is provided a compost prepared according to any of the embodiments described herein pertaining to preparation of a compost.

Oil:

Oils are commonly present in the waste material, and are generally immiscible with aqueous liquids (e.g., an aqueous solution) utilized (according to some embodiments described herein) for separating according to specific gravity. A layer of oil may thus form during the separation process, for example, floating on a surface of an aqueous liquid (as opposed to floating solids which are partially submerged in the aqueous liquid).

In some embodiments of any of the embodiments described herein, the separation process comprises separating oil (i.e., at least a portion of the oil present) from low-density materials described herein (according to any of the embodiments relating to low-density materials), to thereby obtain a separated oil. In some embodiments, separating oil is performed in association with contacting a waste material and/or fraction thereof with an aqueous liquid (according to any of the respective embodiments described herein), for example, an aqueous liquid for separating materials according to specific gravity. In some embodiments, separating the oil comprises skimming the oil off of a surface of an aqueous liquid (e.g., an aqueous liquid contacted with waste material according to any of the respective embodiments described herein).

Herein, the term "oil" refers to a liquid which is immiscible with water, and encompasses substances which are a liquid at at least one temperature in a range of 0° C. to 100° C.

In some embodiments of any of the embodiments described herein, the oils are a liquid at least one temperature in a range of 0° C. to 50° C. In some embodiments of any of the embodiments described herein, the oils are a liquid at 20° C.

In some embodiments of any of the embodiments described herein, oil is separated from low-density materials floating in an aqueous liquid (e.g., prior removal of the low-density materials from the aqueous liquid). Such a separation may be effected, for example, by using a filter configured for selectively separating floating liquids (oils) from floating solid particles (which do not pass through the filter). Additionally or alternatively, such separation may be effected by skimming performed so as to selectively separate low-density materials (e.g., oils) above a surface of the aqueous liquid from materials (e.g., floating solid particles) which are at least partially submerged in the aqueous liquid.

In some embodiments of any of the embodiments described herein, oil is separated from an aqueous liquid after low-density materials floating in an aqueous liquid have been selectively removed from the aqueous liquid (i.e., without removing at least a portion of the oil). Such a separation may be effected, for example, by removing low-density materials from the aqueous liquid using an element (e.g., conveyor) which selectively conveys solids, for example, an element which is permeable to liquids and/or which utilizes friction to convey materials (wherein oils exhibit less friction with the element than solids). Additionally or alternatively, such separation may be effected by passing the aqueous liquid through a suitable oil-water separator.

Separation of oils from the liquid may be performed according to techniques and apparatuses known in the art, for example, electrochemical emulsification; bioremediation; oil-water separators known in the art, including, without limitation, gravity oil-water separators (e.g., API separators, gravity plate separators) and centrifugal oil-water separators; and/or a skimmer.

Examples of suitable skimmers include, without limitation, a weir skimmer, and/or an oleophobic and/or metallic skimmer (e.g., using a rotating element such as a drum, rope, disc and/or belt to adhere to and remove oils). The skimmers (of any type) are optionally configured to cease skimming when oil is not present in sufficient quantities to be skimmed effectively.

In some embodiments of any of the embodiments described herein, oil is skimmed from a first aqueous liquid described herein (e.g., using a skimmer described herein).

In some embodiments of any of the embodiments described herein, a second aqueous liquid described herein is passed through an oil-water separator (e.g., an oil-water separator described herein), to thereby obtain oil. In some such embodiments, separation of oil from the first aqueous liquid is performed, such that an amount of oil available in the second aqueous liquid is relatively low, rendering skimming inefficient.

In some embodiments of any of the embodiments described herein, a liquid removed from a fraction and/or separated material (e.g., by compression and/or drainage, as described herein) is passed through an oil-water separator (e.g., an oil-water separator described herein), to thereby obtain oil.

Oil obtained from different sources (e.g., by different processes for separating oil) may be combined.

In some embodiments of any of the embodiments described herein, the oils comprise lipids released from cells in the waste material during the separation process, for example, upon contact with an aqueous salt solution (e.g., a hypertonic solution) which subjects the cells to osmotic stress.

In some embodiments of any of the embodiments described herein, the method further comprises processing obtained oils to thereby obtain a biofuel. In some embodiments, the biofuel is a liquid biofuel.

Herein, the term "biofuel" refers to a fuel comprising matter derived from plant and/or animal material, and may optionally which further comprise matter which is not derived from plant and/or animal material. A biofuel may be for providing energy for any purpose other than as food, including for example, transportation, heating and/or electricity.

Examples of biofuels which may be obtained by processing oils according to some embodiments described herein include, without limitation, biodiesel fuel, fuel for engines suitable for use of vegetable oil, gasoline, and heating oil.

Herein, the term "biodiesel" refers to biofuel composed primarily (i.e., at least 50 weight percents) of alkyl esters of fatty acids (for example, methyl, ethyl or propyl esters of fatty acids) and/or hydrocarbons derived from plant and/or animal material which are suitable for use as a fuel in a diesel engine (for example, $C_{8-21}$ hydrocarbons). Biodiesel fuel composed primarily of hydrocarbons derived from plant and/or animal material is also known in the art as "green diesel", in order to distinguish it from biodiesel fuel composed primarily of alkyl esters of fatty acids.

In some embodiments, processing oils to obtain biodiesel fuel comprises reacting fatty acid esters in the oils (e.g., triglycerides, phospholipids) with an alcohol, for example, methanol, ethanol and/or propanol, optionally in the presence of a base, for example, methoxide, ethoxide and/or propoxide (e.g., the base being in a form of a sodium and/or potassium salt), to thereby obtain alkyl esters of fatty acids. Such a reaction is also referred to as "transesterification"

In some embodiments, processing oils to obtain biodiesel fuel comprises hydrocracking, hydrogenolysis and/or hydrogenation of the oils.

Processing oils to obtain biodiesel fuel may utilize any process known in the art for obtaining biodiesel fuel from oils (e.g., vegetable oils), including processes comprising transesterification, hydrocracking, hydrogenolysis and/or hydrogenation. Examples of such processes are described, for example, in U.S. Pat. Nos. 4,992,605, 5,705,722, 8,142,527, and 8,859,832, the contents of each of which are incorporated herein in their entirety.

High-density Materials:

In some of any of the embodiments described herein, the separation process according to any of the embodiments described herein further comprises separating at least one metal from other materials in a fraction of high-density materials (e.g., a fraction of high-density materials according to any of the respective embodiments described herein), for example, from a second fraction and/or fifth fraction described herein. In some embodiments, the fraction of high-density materials is a second fraction according to any of the respective embodiments described herein. In some embodiments, the fraction of high-density materials is a fifth fraction according to any of the respective embodiments described herein.

By such separation of a fraction of high-density materials, a metal and/or a high-density non-metallic material may be obtained as a separated material. For example, if the separation results in at least a portion of a metal in a fraction of high-density materials being separated efficiently from other materials in the fraction, a metal is obtained as a separated material; if the separation results in at least a portion of non-metallic material in a fraction of high-density materials being separated efficiently from metals in the fraction, a high-density non-metallic material (e.g., a glass) is obtained as a separated material; and if the separation results in metal in general and non-metallic material in general in a fraction of high-density materials being separated efficiently from each other, a metal and a high-density non-metallic material are both obtained as a separated materials.

In some of any of the embodiments described herein, separation of a metal comprises separation of a magnetic metal (e.g., ferrous metal), for example, by attraction to a magnet.

In some of any of the embodiments described herein, separation of a metal comprises separation of a non-magnetic metal (e.g., non-ferrous metal), for example, by interaction with an eddy current, for example, using an eddy current separator known in the art. In some such embodiments, separation of the non-magnetic metal is performed subsequent to removal of magnetic metal (e.g., as described herein), for example, in order to reduce damage caused by magnetic metal to an eddy current separator.

Herein, a separated material which is a "metal" (also referred to herein interchangeably as "separated metal") refers to a separated material in which at least 60 weight percents by dry weight of the separated material consists of metal.

In some embodiments of any of the embodiments described herein, at least 70 weight percents by dry weight of the separated metal consists of metal. In some embodiments of any of the embodiments described herein, at least 80 weight percents by dry weight of the separated metal consists of metal. In some embodiments of any of the embodiments described herein, at least 90 weight percents by dry weight of the separated metal consists of metal. In some embodiments of any of the embodiments described herein, at least 95 weight percents by dry weight of the separated metal consists of metal. In some embodiments of any of the embodiments described herein, at least 98 weight percents by dry weight of the separated metal consists of metal. In some embodiments of any of the embodiments described herein, at least 99 weight percents by dry weight of the separated metal consists of metal.

Herein, "non-metallic material" (including "high-density non-metallic material") refers to material which is no more than 40 weight percents metal by dry weight.

In some embodiments of any of the embodiments described herein, no more than 30 weight percents of the non-metallic material by dry weight consists of metal. In some embodiments, no more than 20 weight percents of the non-metallic material by dry weight consists of metal. In some embodiments, no more than 10 weight percents of the non-metallic material by dry weight consists of metal. In some embodiments, no more than 5 weight percents of the non-metallic material by dry weight consists of metal. In some embodiments, no more than 2 weight percents of the non-metallic material by dry weight consists of metal. In some embodiments, no more than 1 weight percent of the non-metallic material by dry weight consists of metal.

In some embodiments of any of the embodiments described herein, the separation process further comprises separating high-density non-metallic material, to thereby obtain two or more separated high-density non-metallic materials. Examples of obtainable separated high-density non-metallic materials include, without limitation, silica (e.g., a glass), high-density polymeric material and bone.

In some embodiments of any of the embodiments described herein, at least one of a glass and a high-density polymeric material is obtained.

Separated silica may optionally be processed, for example, by being melted and formed into a silica (e.g., glass) product.

Separated bone may optionally be ground and used, for example, as fertilizer.

Separated high-density polymeric material may optionally be ground and used, for example, as a filler.

In some embodiments of any of the embodiments described herein, high-density non-metallic material is processed by contacting an aggregate comprising a high-density non-metallic material (according to any of the embodiments described herein pertaining to high-density non-metallic material) with a binder to thereby form a concrete. The binder may be any binder known in the art for use in preparing a concrete. In some embodiments, processing comprises grinding the high-density non-metallic material to form the aggregate.

In some embodiments, the concrete is a polymer concrete (i.e., wherein the binder is a polymeric binder).

Without being bound by any particular theory, it is believed that formation of a concrete is a cost-effective use of high-density non-metallic material obtained upon separation of metals, without need for further separation of the high-density non-metallic material into two or more separated high-density non-metallic materials.

According to another aspect of embodiments of the invention, there is provided a concrete (e.g., polymer concrete) prepared according to any of the embodiments described herein pertaining to preparation of a concrete.

Shredding:

Separation of materials may optionally be performed before and/or after shredding, and/or during shredding (e.g., between two stages of shredding).

In some of any of the embodiments described herein, the waste material is a shredded waste material, that is, obtained in a shredded form, for example, waste material has been subjected to crushing (e.g., by a hammer mill). In some embodiments, the shredded waste material is further shredded as described herein.

As used herein, the terms "shred", "shredded" and "shredding" and the further grammatical diversions thereof refer to reduction in size of the solid components of material (e.g., waste material, separated material) by any mechanical means, including chopping, dicing, grinding, crumbling, cutting, tearing and crushing.

A variety of devices are available in the art for shredding waste material and/or fractions thereof, including, without limitation, industrial shredders, grinders, chippers and granulators. Optionally, the device used for shredding is designed to be suitable for handling the presence of hard substances such as metal, glass, clay and stone in waste material, for example, by using blades or plates made of robust materials such as stainless steel or titanium.

Herein, the term "shredder" encompasses all devices configured for shredding, as defined herein.

In some of any of the embodiments described herein, waste material is shredded prior to contacting the waste material with a liquid (e.g., as described herein for, for example, separating according to specific gravity), for example, so as to facilitate separation of different types of material which are attached to one another (e.g., metal attached to plastic) and/or to facilitate escape of gases and entry of liquid to crevices in particles of waste material. In some embodiments, solid particles in the shredded material are less than 50 mm in diameter, optionally less than 20 mm in diameter, when the material is subjected to a separation process (e.g., according to any of the respective embodiments described herein). In some embodiments, the solid particles are less than 10 mm in diameter when the material is subjected to a separation process (e.g., according to any of the respective embodiments described herein).

In some embodiments, shredding prior to removal of materials is effected by hammers (e.g., crushing), for example, by a hammer mill.

Without being bound by any particular theory, it is believed that hammers are relatively resistant to damage associated with a presence of hard materials (e.g., inorganic materials such as mineral, ceramic, glass, metal) in waste material which has not yet been subjected to separation of such materials.

In some of any of the embodiments described herein, a fraction of low-density materials (e.g., a first fraction described herein) is shredded (subsequent to being separated from high-density materials), for example, so as to avoid hard high-density materials (e.g., inorganic materials) which may damage an apparatus effecting the shredding, and/or so that particles of the waste material will not be so small as to interfere with separation (e.g., into a first fraction and second fraction described herein). For example, small particles generally separate according to specific gravity more slowly than do large particles. In some embodiments, the solid particles are at least 2 mm in diameter when materials are subjected to a separation process according to specific gravity. In some embodiments, the solid particles are at least 5 mm in diameter when materials are subjected to a separation process according to specific gravity. In some embodiments, the solid particles are at least 10 mm in diameter when materials are subjected to a separation process according to specific gravity.

In some embodiments of any of the embodiments described herein relating to shredding, shredding of a fraction of low-density materials is effected by cutting (e.g., by blades and/or plates), for example, in an industrial shredder.

Without being bound by any particular theory, it is believed that such a shredding technique is particularly suitable for forming relatively small particles (which may be more suitable for further processing), but may be relatively susceptible to hard high-density materials (e.g., inorganic materials), and therefore suitable for shredding low-density materials in which amounts of such hard materials are reduced, in comparison with waste material prior to the separation process.

In some of any of the embodiments described herein, waste material is shredded prior to the separation process to a relatively large particle size (e.g., at least 10 mm in diameter), for example, using crushing, hammers and/or similar techniques. Subsequent to separation of materials, the fraction of low-density materials is then optionally further shredded to smaller particles (e.g., less than 10 mm in diameter), for example, of a size suitable for further processing (e.g., as described herein).

Each cycle of separating materials (according to any of the respective embodiments described herein) may independently optionally comprise shredding an obtained fraction (optionally a fraction obtained by cycles other than the final cycle), e.g., as described herein. In some embodiments of any of the embodiments described herein, at least one cycle other than the first cycle comprises shredding of an obtained fraction. In some embodiments, the final cycle comprises shredding of an obtained fraction. In some embodiments, each cycle comprises shredding of an obtained fraction.

Processed Polymeric Material:

In some of any of the embodiments described herein, a fraction of low-density materials obtained as described herein is processed to thereby obtain a processed polymeric material. In some embodiments, the fraction is a first fraction according to any of the respective embodiments described herein.

In some of any of the embodiments described herein, processing comprises heating a feedstock which comprises at least a portion of the fraction of low-density materials. Heating may optionally be performed at a temperature suitable to melt, sinter and/or otherwise fuse thermoplastic low-density materials (e.g., polymeric materials), optionally a temperature in a range of 90° C. to 230° C., and optionally from 180° C. to 225° C. The feedstock optionally comprises additional materials, for example, polymeric materials, obtained from a source other than the waste material.

In some of any of the embodiments described herein, a feedstock comprising (optionally consisting of) at least a portion of a first fraction described herein is subjected to processing comprising heating.

In some of any of the embodiments described herein, a feedstock comprising (optionally consisting of) at least a portion of a third fraction described herein is subjected to processing comprising heating. In some embodiments, the third fraction is a separated low-density polymeric material, as described herein.

In some of any of the embodiments described herein, a feedstock comprising (optionally consisting of) a combination of at least a portion of a third fraction described herein and at least a portion of a fourth fraction described herein is subjected to processing comprising heating. In some embodiments, the third fraction is a separated low-density polymeric material, as described herein. In some embodiments, the fourth fraction is a separated lignocellulose or an organic residue remaining after a fermentation process described herein.

In some embodiments of the embodiments, processing comprises subjecting the feedstock to mixing via shear forces, in addition to heating, optionally to mixing and heating simultaneously.

Optionally, shear forces are generated by a compounder, such as, without limitation, an extruder, an internal mixer (a Banbury® mixer), a co-kneader, and/or a continuous mixer etc.

The feedstock is optionally subjected to heating without being dried beforehand.

In some of any of the embodiments described herein, at least 50 weight percents of the dry weight of the feedstock is a separated material obtained by separating materials in a waste material according to specific gravity, as described herein. In some embodiments, at least 80 weight percents of the dry weight of the feedstock is a separated material. In some embodiments, at least 90 weight percents of the dry weight of the feedstock is a separated material. In some embodiments, at least 95 weight percents of the dry weight of the feedstock is a separated material. In some embodiments, at least 98 weight percents of the dry weight of the feedstock is a separated material. In some embodiments, at least 99 weight percents of the dry weight of the feedstock is a separated material.

In some of any of the embodiments pertaining to a method of processing waste material as described herein, the feedstock (prior to mixing and heating) has a water content of at least 15 weight percents. In some embodiments, the feedstock has a water content of at least 20 weight percents. In some embodiments, the feedstock has a water content of at least 40 weight percents. In some embodiments, the feedstock has a water content of at least 60 weight percents.

The origin of water in the feedstock may optionally be the water content of a waste material, an aqueous liquid used for separation according to specific gravity (e.g., as described herein), and/or water added to a separated material.

According to another aspect of embodiments of the invention, there is provided a processed polymeric material prepared by processing (as described herein) material obtained by separating waste material (as described herein).

System:

According to another aspect of embodiments of the invention there is provided a system for separating a waste material.

The system comprises at least one separator configured for separating materials in waste material according to specific gravity (e.g., according to any of the respective embodiments described herein), so as to obtain at least two fractions, the fractions comprising at least a first fraction of low-density materials (e.g., according to any of the respective embodiments described herein) and second fraction of high-density materials (e.g., according to any of the respective embodiments described herein).

Herein, the term "separator" (except when used in the context of a longer name, such as "oil-water separator", "metal separator" and the like) refers to a device containing a liquid selected such that a portion of the waste material sinks and another portion does not sink (e.g., according to any of the respective embodiments described herein), thereby obtaining the first and second fractions.

In some embodiments of any of the embodiments pertaining to a system, the system is configured for effecting a separation process according to any of the respective embodiments described herein.

In some embodiments of any of the embodiments pertaining to a system, the at least one separator comprises a first separator containing a first aqueous liquid and a second separator containing a second aqueous liquid. The first aqueous liquid, the second aqueous liquid, and combinations thereof may each be according to any of the respective embodiments described herein. The first separator is configured for separating waste material according to specific gravity to thereby obtain a first fraction and second fraction (e.g., according to any of the respective embodiments described herein), and the second separator is configured for receiving a fraction from the first separator (e.g., the separators being in communication) and for separating the fraction received from the first separator according to specific gravity (e.g., according to any of the respective embodiments described herein), thereby obtaining a third fraction of low-density materials (e.g., according to any of the respective embodiments described herein), a fourth fraction of intermediate-density materials (e.g., according to any of the respective embodiments described herein) and a fifth fraction of high-density materials (e.g., according to any of the respective embodiments described herein).

In some embodiments of any of the embodiments pertaining to a system described herein, one or more separator(s) is configured for conveying one or more fractions and/or separated materials (e.g., a first fraction of low-density materials, second fraction of high-density material and/or an oil, according to any of the respective embodiments described herein) to another component of the system. In such embodiments, the separator(s) may be configured for removing materials which sink in the liquid and/or for removing materials which float in the liquid.

In some embodiments of any of the embodiments pertaining to a system described herein, the system further comprises at least one apparatus configured for obtaining a low-density polymeric material, high-density polymeric material, metal, glass, oil and/or lignocellulose as a separated material, according to any of the respective embodiments described herein. In some embodiments, the at least one apparatus is configured for obtaining at least two of the aforementioned separated materials, according to any of the respective embodiments described herein. Optionally, one apparatus is configured for obtaining one separated material and another apparatus is configured for obtaining another separated material.

In some embodiments of any of the embodiments pertaining to a system described herein, the system further comprises at least one apparatus and/or subsystem configured for processing at least a portion of an obtained fraction (e.g., first fraction or second fraction) described herein to thereby obtain at least one processed material described herein.

In some embodiments of any of the embodiments pertaining to a system described herein, the system comprises a subsystem configured for processing separated oil, for example, to thereby obtain a biofuel (e.g., according to any of the embodiments described herein pertaining to such processing).

In some embodiments of any of the embodiments described herein, the system comprises a bioreactor in communication with at least one separator described herein, the bioreactor being configured for subjecting at least a portion of a fraction of materials (e.g., first fraction and/or fourth fraction) to a fermentation process according to any one of the respective embodiments described herein (e.g., in the section relating to fermentation). In some embodiments, the system comprises an apparatus (optionally a part of a bioreactor) configured for collecting an organic residue and obtaining a compost from the organic residue (optionally by mixing additional materials with the organic residue), as described herein.

In some embodiments of any of the embodiments described herein, the system comprises an apparatus in communication with at least one separator, the apparatus being configured for receiving a fraction of high-density material (e.g., second fraction and/or fifth fraction) according to any of the respective embodiments described herein, and for separating the fraction to thereby obtain a separated metal and/or high-density non-metallic material, according to any of the respective embodiments described herein. Optionally, the apparatus comprises an eddy current separator.

In some embodiments of any of the embodiments described herein, the system comprises an apparatus configured for separating high-density non-metallic material in accordance with any of the respective embodiments described herein.

In some embodiments of any of the embodiments described herein, the system comprises an apparatus configured for grinding at least a portion of the high-density non-metallic material into an aggregate and/or for preparing a concrete from the an aggregate comprising at least a portion of the high-density non-metallic material, in accordance with any of the respective embodiments described herein.

In some embodiments of any of the embodiments described herein, the system comprises an apparatus configured for preparing a feedstock which comprises at least a portion of a third fraction and at least a portion of a fourth fraction (optionally an organic reside from a bioreactor) according to any of the respective embodiments described herein, for example, by receiving and combining the fractions in pre-determined proportions.

In some embodiments of any of the embodiments described herein, the system comprises an apparatus configured for processing at least a portion of a first fraction of low-density materials in accordance with any of the respective embodiments described herein. In some embodiments, the apparatus is configured for processing by heating a feedstock comprising low-density materials in accordance with any of the respective embodiments described herein. In some such embodiments, the feedstock comprises at least a portion of a third fraction and/or at least a portion of a fourth fraction (e.g., organic residue from a bioreactor) in accordance with any of the respective embodiments described herein.

In some embodiments of any of the embodiments pertaining to a system described herein, the system is configured for separating a shredded waste material (e.g., as described herein), for example, waste material subjected to crushing (e.g., by a hammer mill).

In some embodiments of any of the embodiments pertaining to a system described herein, the system further comprises at least one shredder configured for shredding the waste material (e.g., as described herein).

In some embodiments of any of the embodiments pertaining to a system described herein, the system is configured such that at least one separator and at least one shredder are in operative communication in tandem, such that the system is configured for performing at least one separation according to specific gravity and at least one shredding process in a desired sequence (e.g., a sequence described herein).

In some embodiments of any of the embodiments pertaining to a system described herein, the system is configured for shredding the waste material prior to contacting the waste material with the liquid of a separator (e.g., as described herein).

In some embodiments of any of the embodiments pertaining to a system described herein, the system is configured for shredding at least a portion of a first fraction, third fraction and/or fourth fraction of low- or intermediate-density materials according to any of the respective embodiments described herein, for example, as obtained by contacting the waste material with the liquid of a separator. Such a fraction may be a fraction for which further separation of materials (e.g., in a separator as described herein) is intended; or a final separated material, for which no further separating is intended.

In some embodiments of any of the embodiments pertaining to a system described herein, the system comprises at least one plurality of separators and/or at least one plurality of shredders configured to operate in parallel. In such embodiments, the plurality of separators and/or plurality of shredders may be configured to perform essentially the same operation, which may allow, for example, a greater throughput of material for such an operation.

In some embodiments of any of the embodiments pertaining to a system described herein, the system further comprises a monitor adapted for monitoring a composition and/or specific gravity of the liquid in one or more separators. In some embodiments, the monitor is configured to adjust a composition and/or specific gravity of the liquid, for example, for maintaining a specific gravity at a predetermined value (e.g., within a predetermined range). In some embodiments, the monitor is configured for controlling entry of water and/or additional substance such as a solute (e.g., a salt described herein) into the separator liquid, to thereby adjust the composition and/or specific gravity of the liquid.

In some embodiments of any of the embodiments pertaining to a system described herein, the system comprises at least one oil-water separator (e.g., an oil-water separator described herein) configured for separating oil from low-density materials and/or from a liquid of one or more separators, to thereby obtain an oil, according to any of the respective embodiments described herein (e.g., in the section herein relating to oil). Such an apparatus may be configured to remove oil from a separator (e.g., by skimming) and/or from liquid processed outside a separator (e.g., liquid separated from a separated material outside of a separator (e.g., according to any of the respective embodiments described herein).

In some such embodiments, the oil-water separator(s) comprises is a skimmer (e.g., a skimmer described herein), for example, a skimmer configured for separating oil from a liquid of a first separator.

In some embodiments of any of the embodiments pertaining to a system described herein, the system further comprises an apparatus configured for separating at least a portion of liquid from a fraction and/or separated material by compression. In some embodiments, the apparatus comprises a screw press. The liquid being separated may comprise, for example, a combination of liquid used for separating according to specific gravity (according to any of the respective embodiments described herein) and liquid derived from the source waste material (e.g., aqueous liquids and oils).

In some embodiments of any of the embodiments pertaining to a system described herein, an apparatus configured for separating liquids (e.g., oil) from a separated material by compression is configured to receive material from at least one shredder described herein. In some embodiments, the apparatus comprises a screw press.

In some embodiments of any of the embodiments pertaining to a system described herein, the system comprises at least one reservoir for collecting oil-containing liquid derived from the waste material, the reservoir being in operative communication with at least one component of the system which handles waste material and/or a material derived therefrom. In some embodiments, the reservoir is in communication with at least one shredder adapted for conveying liquid from waste material and/or a separated material derived therefrom undergoing shredding to the reservoir (e.g., being adapted for draining liquid).

In some embodiments of any of the embodiments pertaining to a system described herein, the reservoir is configured for separating oil from at least a portion of the liquid (e.g., as described herein).

FIG. 3 is a schematic illustration of a system 100 for separating waste material, according to some embodiments of the present invention. System 100 comprises a separator 110, and optionally and preferably further comprises a second separator 150, for separating material into at least two fractions, according to specific gravity.

In some embodiments, separator 110 separates waste material into a first fraction comprising a low-density material which does not sink in an aqueous liquid in separator 110 (optionally a salt solution) and a second fraction comprising a high-density material which sinks in the liquid.

In some embodiments, system 100 comprises a second separator 150, which receives material from first fraction and/or second fraction from separator 110, optionally via conduit 132. System 100 is optionally configured such that material from either the first fraction or the second fraction may be received by separator 150, in a controllable and reversible manner. The material may be received after passing through shredder 130 (as depicted in FIG. 3) which is optionally connected to separator 110 by conduit 114, although passage of material from separator 110 to separator 150 without passing through shredder 130 is also contemplated.

In some embodiments, separator 150 separates material received directly or indirectly from separator 110 into a fraction comprising a low-density material which does not sink in an aqueous liquid in separator 150 (optionally water) and a fraction comprising a high-density material which sinks in the liquid. In some embodiments, separator 150 separates material from a first fraction into a third fraction comprising a low-density material which does not sink in an aqueous liquid in separator 150 (optionally water) and a fourth fraction comprising an intermediate-density material which sinks in the liquid. Additionally or alternatively, separator 150 separates material from a second fraction into a fifth fraction comprising a high-density material which sinks in an aqueous liquid in separator 150 (optionally a salt solution) and a fourth fraction comprising an intermediate-density material which does not sink in the liquid.

In some embodiments, system 100 comprises a bioreactor 160, which receives material from separator 150 (as depicted in FIG. 3) and/or separator 110 (not shown), optionally via conduit 152. The material may be a lignocellulose-rich fraction, optionally an intermediate-density material received from separator 150. Bioreactor 160 is configured for metabolism of material into a biogas and/or ethanol.

In some embodiments, system 100 comprises one or more of oil-water separator 140, each of which may be in functional communication with any one or more of separator 110, shredder 130 and separator 150.

In some embodiments, separator 110 is in functional communication with oil-water separator 140 (optionally via conduit 116), for separating oil from an aqueous liquid in separator 110.

In some embodiments, separator 150 is in functional communication with oil-water separator 140 (optionally via conduit 154), for separating oil from an aqueous liquid in separator 150.

In some embodiments, oil-water separator 140 is configured to receive liquid from shredder 130, optionally conduit 134. Shredder 130 is optionally configured for removing liquid from material being shredded, for example, by compression and/or drainage.

In some embodiments, system 100 comprises metal separator 120, optionally comprising a magnetic separator and/or eddy current separator, for receiving a material from separator 110, preferably a high-density material from the second fraction and separating at least one metal from non-metallic material.

In some embodiments, system 100 further comprises inlets and outlets in some or all of its components, for allowing communication between the components.

In some embodiments, system 100 further comprises collector units for collecting the separated materials or the processed materials as described herein.

As used herein the term "about" refers to ±10%.

The terms "comprises", "comprising", "includes", "including", "having" and their conjugates mean "including but not limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical arts.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non-limiting fashion.

Example 1

General Procedure for Separating Waste Material According to Specific Gravity

A general procedure for separating waste material according to specific gravity according to some embodiments of the present invention is shown in FIG. 1.

In some embodiments, the procedure is performed using a system such as described and exemplified in FIG. 3 and/or FIG. 4.

Waste material 10 is provided, optionally "wet" waste material, i.e., waste material which has not been subjected to drying, and optionally wet substantially unsorted waste material (SUW). The waste material is preferably domestic waste material, e.g., collected from private households. Optionally, the waste material has been subjected to preliminary processing procedures (e.g., at a waste disposal facility), such as crushing (e.g., by a hammer mill), and/or removal of magnetic materials.

Waste material 10 is subjected to separation according to specific gravity 20 (by contacting the waste material 10 with a liquid), resulting in separation of waste material 10 into a first fraction of low-density materials 12 and a second fraction of high-density materials 14. First fraction 12 (and optionally second fraction 14) is subjected to shredding 25, resulting in a shredded material, which may optionally be subjected to one or more additional cycles of separation of waste material 10 into a first fraction of low-specific gravity materials 12 and a second fraction of high-specific gravity materials 14, and optionally shredding the first fraction 12 and/or second fraction 14.

The second fraction 14 may optionally be further separated so as to extract useful and/or valuable materials such as metals (e.g., iron, gold) and silica and/or glass (e.g., for use as filler).

Additional cycles of separation 20 may be according to the same distinction between low-specific gravity material and high-specific gravity material (e.g., using the same specific gravity of liquid used for separation) as in a previous cycle or a different distinction between low-specific gravity material and high-specific gravity material (e.g., using a different specific gravity of liquid used for separation). Use of a different distinction between low-specific gravity material and high-specific gravity material may result in separation into a third fraction of low-density materials (comprising materials from first fraction 12 of each of two different cycles of separation 20), a fourth fraction of intermediate-density materials (comprising materials which are from fraction 12 for one cycle of separation 20, and from second fraction 14 for another cycle of separation 20) and fifth fraction of high-density materials (comprising materials from second fraction 12 of each of two different cycles of separation 20).

Additional cycles of separation 20 and shredding 25 optionally comprise finer shredding of material than in a previous cycle.

Optionally, the first cycle of separation 20 and shredding 25 comprises removing high-specific gravity inorganic materials which may interfere with shredding 25, followed by at least one additional cycle of separation 20.

Optionally, additional cycle of separation 20 is made more effective due to the previous shredding 25, which facilitates, for example, removal of air pockets from the material and/or dismantling of waste material particles into their component materials.

Optionally, shredding 25 is performed in such a manner as to remove liquid (e.g. liquid absorbed during separation 20) from the separated material being shredded, for example, by compression (e.g., using a screw press) and/or drainage of the material during shredding. Optionally, shredding 25 is performed in such a manner after each cycle of separation 20.

Additional materials (e.g., as described herein) may optionally be added at any stage, during one or more cycles described herein, for example, to waste material 10, to first fraction 12 and/or to second fraction 14 prior to and/or subsequent to shredding 25.

Separated material obtained according to this general procedure may optionally be subjected to a procedure for processing a feedstock by mixing and heating, e.g., the procedure described in Example 2.

Example 2

General Procedure for Separating Waste Material

A general procedure 200 for separating waste material according to some embodiments of the present invention is shown in FIG. 2. In general, procedures are indicated by dashed lines, materials by full lines, and separated materials of particular interest by bold lines. In some embodiments, general procedure 200 includes, but is not limited to, the general procedure shown in FIG. 1.

Waste material 210 (optionally as described for waste material 10 in Example 1) is subjected to separation in salt solution 215 (by contacting the waste material 210 with a salt solution), resulting in separation of waste material 210 into a first fraction of low-density materials 230 and a second fraction of high-density materials 220. Separation in salt solution 215 may optionally utilizes a salt solution (e.g., sodium chloride solution) having a specific gravity of at least 1.05, optionally at least 1.07, optionally at least 1.10, optionally at least 1.15 and optionally at least 1.20, as described herein. Optionally, separation in salt solution 215 further comprises obtaining oil-rich liquid 240 (comprising of or consisting of oil) from a surface of the salt solution, for example, by skimming. First fraction 230 is optionally subjected to shredding 232, resulting in shredded low-density materials.

First fraction 230, which is wet, is then subjected to liquid removal 234, to thereby obtain partially wet first fraction 250 and liquids 255. Liquid removal 234 optionally comprises compression (e.g., by screw press) and/or draining (driven by gravity and/or compression).

Partially wet first fraction 250 is subjected to separation in water 252 (by contacting material of fraction 250 with water), resulting in separation of material of fraction 250 into a third fraction of low-density materials 270 (optionally low-density polymeric material, as described herein) and a fourth fraction of intermediate-density materials 260 (optionally separated lignocellulose as described herein). Separation in water 252 may optionally utilizes an aqueous liquid (e.g., pure water or dilute aqueous solution) having a specific gravity of no more than 1.03, optionally no more than 1.02, optionally no more than 1.01, and optionally no more than 1.00, as described herein. Optionally, separation in water 252 further comprises obtaining oil-rich liquid 272 (comprising of or consisting of oil), for example, by skimming a surface of the water.

Separation in salt solution 215 and separation in water 252 are each optionally performed using a system as described in FIG. 4, containing the appropriate liquids.

Fourth fraction 260 is optionally subjected to fermentation process 262, which is adapted to result in a fermentation product such as ethanol 264 and/or biogas 266. Material from fourth fraction 260 which is not converted to a fermentation product such as ethanol 264 and/or biogas 266 remains as organic residue 268. Fourth fraction 260 and organic residue 268 may each be optionally used to form a compost.

Third fraction 270 is optionally processed by heating a feedstock comprising thirst fraction 270, to produce a relatively homogeneous processed polymeric material. The feedstock may optionally comprise additional materials, including fourth fraction 260 and/or organic residue 268. Third fraction 270, fourth fraction 260 and/or organic residue 268 may be included in pre-determined proportions in the feedstock, the proportions depending on the desired properties of the processed material and/or the relative cost effectiveness of different combinations of third fraction 270, fourth fraction 260 and organic residue 268.

Second fraction 220 may optionally be subjected to metal separation 222, optionally using an eddy current separator, to thereby obtain separated metal 224 and high-density non-metallic materials 226. Materials 226 may optionally be further separated, for example, to obtain separated high-density polymeric material and separated non-polymeric material (e.g., glass); and or used as an aggregate in a concrete (e.g., polymer concrete).

Oil-rich liquid 240 and/or 272, and/or liquids 255 are optionally subjected to oil-water separation 280 to obtain separated oil 282 and aqueous liquid 284. If oil-rich liquid 240 and/or 272 is sufficiently free of water, oil 282 may be optionally obtained therefrom without oil-water separation 280. In addition, if liquids 280 does not comprise sufficient amount of oil, oil 282 may optionally be obtained from oil-rich liquid 240 and/or 272 alone. Liquids 240, 272 and/or 255 may optionally undergo oil-water separation 280 in the same manner (e.g., using the same type of oil-water separator), optionally after being combined; or in different manners (e.g., using different types of oil-water separators) selected to be suitable for the composition of each of liquids 240, 272 and/or 255.

Example 3

System for Separating Waste Materials According to Specific Gravity

An exemplary system for separating waste materials according to specific gravity according to some embodiments of the invention is shown in FIG. 4. The system is may optionally be incorporated within a larger system for separating and/or processing waste material, as described herein.

The system comprises a container 300 which is at least partially filled with liquid 310, and optionally a stirrer 350 (e.g., a paddle wheel) within container 300 or in communication with container 300. Liquid 310 is selected to have a specific gravity suitable for separating waste material (e.g., in a range of from 1.00 to 2.50). Liquid 310 is optionally an aqueous solution. Container 300, along with its associated devices (as described herein), is also referred to as a "separator".

Container 300 is configured to allow waste material (optionally shredded waste material) to enter (as indicated by arrow 320), and to allow some waste material at surface 315 of the liquid 310, and optionally additional material in liquid 310 which does not sediment (e.g., is not at the bottom of container 300), to exit container 300 via outlet 330 (as indicated by arrow 325).

Optional conveyor 365 is located at or near surface 315, and is configured to convey a first fraction of material at or near surface 315 of the liquid 310 out of container 300 via outlet 330. For example, material floating at surface 315 comes into contact with conveyor 365, allowing conveyor 365 to convey the material.

Optional conveyor 360 is configured to convey a second fraction of material at or near bottom of container 300 (e.g., sediment) out of container 300. Conveyor 360 may optionally be configured to raise material above surface 315 before exiting container 300.

Conveyor 365 and/or conveyor 360 optionally comprise teeth and/or grooves and/or the like (not depicted), configured for grabbing material, so as to facilitate conveying.

Outlet 330 is optionally configured to remove, optionally by gravity and/or centrifugal force, at least some liquid 310 which adheres to and/or is absorbed by materials of the first fraction exiting via outlet 330, or otherwise leaks from container 300 into outlet 330. Liquid 310 which is removed in outlet 330 may optionally be returned to container 300 via optional conduit 340.

Liquid 310 is optionally a solution (optionally a salt solution) or a suspension, comprising a solvent (optionally water) and an additional substance (e.g., a solute and/or a suspended substance).

The system is optionally configured to adjust a specific gravity of said liquid to a predetermined value (e.g., a value within a predetermined range).

Optional reservoir(s) 380 comprises water and/or additional substance, which enter container 300 via conduit(s) 390 to replenish and/or adjust a composition and/or specific gravity of liquid 310.

Optional monitor 370 is in communication with container 300, and monitors a composition and/or specific gravity of liquid 310. Monitor 370 is optionally configured to control entry of water and/or additional substance from reservoir(s) 380 into container 300, so as to control a composition and/or specific gravity of liquid 310.

Optional container 395 receives material of the first fraction exiting container 300 via outlet 330 (as indicated by arrow 325), and is filled with a liquid (not shown) adapted for rinsing off at least some liquid 310 which adheres to and/or is absorbed by materials of the first fraction exiting via outlet 330.

In some embodiments, conveyor 315 extends into outlet 330, and optionally into container 395.

In some embodiments, an additional conveyor (not shown) conveys material through outlet 330 and/or container 395.

Outlet 330 and/or container 395 is optionally configured for conveying material of the first fraction to an apparatus for shredding the material (e.g., shredding to a finer particle size) and/or to an apparatus for heating and mixing a feedstock derived from waste material as described herein.

Container 300 and/or container 395 is optionally in communication with a filtration apparatus (not shown), optionally a reverse osmosis filtration apparatus, adapted for filtering out solutes and/or small particles of material. In some embodiments, a filtration apparatus in communication with container 395 is adapted for filtering residual solute of liquid 310 out of the liquid in container 395. In some embodiments, a filtration apparatus in communication with container 300 is adapted for filtering small particles of material out of liquid 310 in container 300.

In some embodiments, a system comprises a plurality (e.g., a pair) of containers 300 (e.g., a plurality of separators), configured for operating in parallel and/or in tandem, each configured as described herein (e.g., with conveyors 360 and 365, stirrer 350 and outlet 330), being in communication with a single container 395. Such a configuration may allow for continuous operation of the system when one container 300 is not available for separating waste materials (e.g., due to maintenance and/or removal of waste materials therefrom) and/or for performing multiple cycles of separation (e.g., using liquids with different specific gravities).

Example 4

Effect of Hypertonic Solution on Biomass in Waste Material 6 grams of fresh organic waste (carrot, cucumber, banana peels) was placed in samples of 60 ml fresh water or 60 ml of salt water with about 20 weight percents, and incubated at room temperature for 3 hours. Filtrates of each sample were then analyzed by $^{13}$C-NMR spectroscopy, performed as described in Example 7.

As shown in FIGS. 5A and 5B, the filtrate from the salt solution exhibited NMR signals in a range of from 60-100 ppm (FIG. 5A), typical of carbohydrates such as glucose and xylose, whereas no such signals were observed for the filtrate obtained from fresh water (FIG. 5B).

These results indicate that the use of hypertonic solutions to separate waste material breaks cell walls and facilitates release of carbohydrates.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A method of separating waste material which is municipal solid waste comprising a low-density polymeric material, lignocellulose, and a high-density polymeric material, the method comprising subjecting the waste material to a separation process according to specific gravity, wherein the separation process comprises contacting the waste material with an aqueous liquid selected such that a portion of said waste material sinks and another portion does not sink,
wherein said separation process comprises contacting the waste material with a first aqueous liquid selected such that a portion of said waste material sinks, thereby obtaining a first fraction which comprises a low-density material and a second fraction which comprises a high-density material, and further contacting at least one of said first fraction and said second fraction with a second aqueous liquid selected such that a portion of said fraction sinks, thereby obtaining a third fraction comprising a low-density material which does not sink in either of said aqueous liquids, a fourth fraction comprising an intermediate-density material which sinks in one of said aqueous liquids, and a fifth fraction comprising a high-density material which sinks in both of said aqueous liquids,
wherein said low-density material in said third fraction comprises a separated low-density polymeric material, said intermediate-density material comprises a separated lignocellulose, and said high-density material in said fifth fraction comprises said high-density polymeric material,
and wherein at least one of said first aqueous liquid and said second aqueous liquid comprises an aqueous salt solution,
thereby separating the waste material to a plurality of separated materials.

2. The method of claim 1, wherein said plurality of separated materials further comprise one or more materials selected from a metal, a glass, and an oil.

3. The method of claim 1, further comprising processing at least one of said separated materials to thereby obtain at least one processed material selected from a processed polymeric material, a compost, a biogas, ethanol, a biodiesel fuel and a concrete.

4. The method of claim 1, wherein a specific gravity of said aqueous liquid which comprises said aqueous salt solution is at least 1.05.

5. The method of claim 4, wherein a specific gravity of one of said first aqueous liquid and said second aqueous liquid is at least 1.05, and a specific gravity of the other of said first aqueous liquid and said second aqueous liquid is no more than 1.01.

6. The method of claim 1, further comprising subjecting at least a portion of said fourth fraction which comprises an intermediate-density material to a fermentation process.

7. The method of claim 6, wherein said fermentation process produces a biogas and/or ethanol.

8. The method of claim 6, further comprising processing at least a portion of an organic residue remaining after said fermentation process to thereby obtain a compost.

9. The method of claim 1, further comprising separating oil from said fraction which comprises a low-density material, to thereby obtain a separated oil.

10. The method of claim 9, further comprising processing said oil to thereby obtain a biodiesel fuel.

11. The method of claim 1, wherein said high-density material comprises at least one of a metal and a high-density non-metallic material, the method further comprising separating said high-density material to thereby obtain a separated metal and/or a separated high-density non-metallic material.

12. The method of claim 11, further comprising contacting an aggregate comprising said high-density non-metallic material with a binder to thereby form a concrete.

13. The method of claim 1, further comprising processing a low-density material separated from the waste material to thereby obtain a processed polymeric material.

14. The method of claim 13, wherein said processing comprises heating a feedstock comprising said low density material.

15. The method of claim 13, wherein said low-density material is processed together with an organic residue remaining after a fermentation process.

16. The method of claim 1, further comprising shredding at least a portion of said first fraction subsequent to said contacting the waste material with said first aqueous liquid.

17. A system for separating a waste material according to claim 1, the system including:
at least one separator configured for separating materials in the waste material according to specific gravity so as to obtain at least two fractions, said fractions comprising at least a first fraction which comprises a low density material and at least a second fraction which comprises a high-density material, said separator containing an aqueous liquid selected such that a portion of said waste material sinks and another portion does not sink, thereby obtaining said first fraction and said second fraction.

18. The system of claim 17, further comprising at least one apparatus configured for processing at least a portion of said first fraction or said second fraction to thereby obtain at least one processed material selected from a processed polymeric material, a compost, a biogas, ethanol, a biodiesel fuel and a concrete.

19. The system of claim 17, wherein a specific gravity of said aqueous liquid is at least 1.05.

20. The system of claim 17, wherein said at least one separator comprises a first separator containing a first aqueous liquid and a second separator containing a second aqueous liquid, said first separator and said second separator being in communication, and said second separator being configured for receiving at least one fraction from said first separator, and for separating said fraction received from said first separator according to specific gravity, said second aqueous liquid being selected such that a portion of said fraction received from said first separator sinks, thereby obtaining a third fraction comprising a low-density material which does not sink in either of said aqueous liquids, a fourth fraction comprising an intermediate-density material which sinks in one of said aqueous liquids, and a fifth fraction comprising a low-density material which sinks in both of said aqueous liquids.

21. The system of claim 20, wherein a specific gravity of one of said first aqueous liquid and said second aqueous liquid is at least 1.05, and a specific gravity of the other of said first aqueous liquid and said second aqueous liquid is no more than 1.01.

22. The system of claim 20, wherein said second separator is configured for obtaining a separated lignocellulose, said intermediate-density material comprising said lignocellulose.

23. The system of claim 20, wherein said second separator is configured for obtaining a separated low-density polymeric material, said low-density material in said third fraction comprising said low-density polymeric material.

24. The system of claim 20, further comprising a bioreactor in communication with said second separator, said bioreactor being configured for subjecting at least a portion of said fourth fraction which comprises an intermediate-density material to a fermentation process.

25. The system of claim 24, wherein said bioreactor is configured for obtaining a biogas and/or ethanol.

26. The system of claim 24, comprising an apparatus configured for collecting an organic residue in said bioreactor and processing collected organic residue to thereby obtain a compost.

27. The system of claim 17, comprising an oil-water separator configured for separating oil from said fraction which comprises a low-density material, to thereby obtain a separated oil.

28. The system of claim 27, further comprising a subsystem configured for processing said oils to thereby obtain a biodiesel fuel.

29. The system of claim 17, comprising an apparatus in communication with said separator, said apparatus being configured for receiving said high-density material from said separator, wherein said high-density material comprises at least one of a metal and a high-density non-metallic material, and for separating said high-density material, to thereby obtain a separated metal and/or a separated high-density non-metallic material.

30. The system of claim 17, comprising an apparatus configured for processing a low-density material separated from the waste material, to thereby obtaining a processed polymeric material.

31. The system of claim 30, wherein said processing comprises heating a feedstock comprising said low-density material.

32. The system of claim 17, further comprising a shredder configured for shredding at least a portion of said first fraction subsequent to contacting the waste material with said aqueous liquid.

33. The system of claim 17, wherein said aqueous liquid comprises an aqueous salt solution.

* * * * *